United States Patent
Carrier, Jr. et al.

(10) Patent No.: US 11,589,957 B2
(45) Date of Patent: Feb. 28, 2023

(54) METHODS AND APPARATUSES FOR DENTAL IMAGES

(71) Applicant: Align Technology, Inc., San Jose, CA (US)

(72) Inventors: Maurice K. Carrier, Jr., Cary, NC (US); Phillip Thomas Harris, Cary, NC (US); Sergey Vinnichenko, Cary, NC (US); Samuel Blanco, Santa Clara, CA (US); Aleksandr Sergeevich Karsakov, Moscow (RU); Sebastien Hareng, San Jose, CA (US); Leon Rasovsky, Sunnyvale, CA (US)

(73) Assignee: Align Technology, Inc., San Jose, CA (US)

(*) Notice: Subject to any disclaimer, the term of this patent is extended or adjusted under 35 U.S.C. 154(b) by 0 days.

(21) Appl. No.: 17/882,522

(22) Filed: Aug. 5, 2022

(65) Prior Publication Data

US 2022/0369916 A1  Nov. 24, 2022

Related U.S. Application Data

(63) Continuation of application No. 17/543,637, filed on Dec. 6, 2021, which is a continuation of application
(Continued)

(51) Int. Cl.
| | |
|---|---|
| *G09G 3/30* | (2006.01) |
| *A61C 7/00* | (2006.01) |
| *A61C 19/04* | (2006.01) |
| *G06T 7/13* | (2017.01) |
| *G06V 20/50* | (2022.01) |
| *G06V 10/764* | (2022.01) |

(Continued)

(52) U.S. Cl.
CPC ............... *A61C 7/002* (2013.01); *A61B 1/24* (2013.01); *A61B 5/6898* (2013.01); *A61C 9/0053* (2013.01); *A61C 19/04* (2013.01); *G06T 7/0012* (2013.01); *G06T 7/13* (2017.01); *G06V 10/764* (2022.01); *G06V 20/50* (2022.01); *H04N 5/2256* (2013.01); *H04N 5/2354* (2013.01); *H04N 5/272* (2013.01); *G06T 2207/30036* (2013.01); *G06T 2207/30168* (2013.01); *G06V 2201/03* (2022.01); *G16H 40/63* (2018.01)

(58) Field of Classification Search
CPC ....... A61C 7/002; A61C 9/0053; A61C 19/04; G06T 2207/30036; G06V 10/764
USPC .......................................................... 345/77
See application file for complete search history.

(56) References Cited

U.S. PATENT DOCUMENTS 6,854,973 B2   2/2005  Butcher et al.
10,159,541 B2 * 12/2018  Bindayel .............. A61B 5/6802
(Continued)

*Primary Examiner* — Gordon G Liu
(74) *Attorney, Agent, or Firm* — Shay Glenn LLP

(57) ABSTRACT

Described herein are methods and apparatuses to obtain an image, or a set of images, of a patient's teeth from one or more predetermined viewing angles. These methods and apparatuses may include the use an overlay comprising an outline of teeth for each predetermined viewing angle. The overlay may be used for automatically capturing, focusing and/or illuminating the teeth. Also described herein are methods and apparatuses for using a series of images of the patient's teeth including a set of predetermined views to determine if a patient is a candidate for an orthopedic procedure.

30 Claims, 17 Drawing Sheets

Related U.S. Application Data

No. 16/952,072, filed on Nov. 18, 2020, now Pat. No. 11,191,617, which is a continuation of application No. 16/827,594, filed on Mar. 23, 2020, now Pat. No. 10,932,885, which is a continuation of application No. 15/803,718, filed on Nov. 3, 2017, now Pat. No. 10,595,966.

(60) Provisional application No. 62/417,985, filed on Nov. 4, 2016.

(51) Int. Cl.
| | | |
|---|---|---|
| *A61B 1/24* | (2006.01) | |
| *A61B 5/00* | (2006.01) | |
| *G06T 7/00* | (2017.01) | |
| *H04N 5/225* | (2006.01) | |
| *H04N 5/235* | (2006.01) | |
| *H04N 5/272* | (2006.01) | |
| *A61C 9/00* | (2006.01) | |
| *G16H 40/63* | (2018.01) | |

(56) References Cited

U.S. PATENT DOCUMENTS

| | | | |
|---|---|---|---|
| 2004/0029068 A1* | 2/2004 | Sachdeva | G16H 50/50 433/24 |
| 2009/0174786 A1* | 7/2009 | Joseph | H04N 5/23222 348/222.1 |
| 2016/0246936 A1* | 8/2016 | Kahn | G16H 40/63 |
| 2016/0256035 A1* | 9/2016 | Kopelman | G06T 7/13 |

* cited by examiner

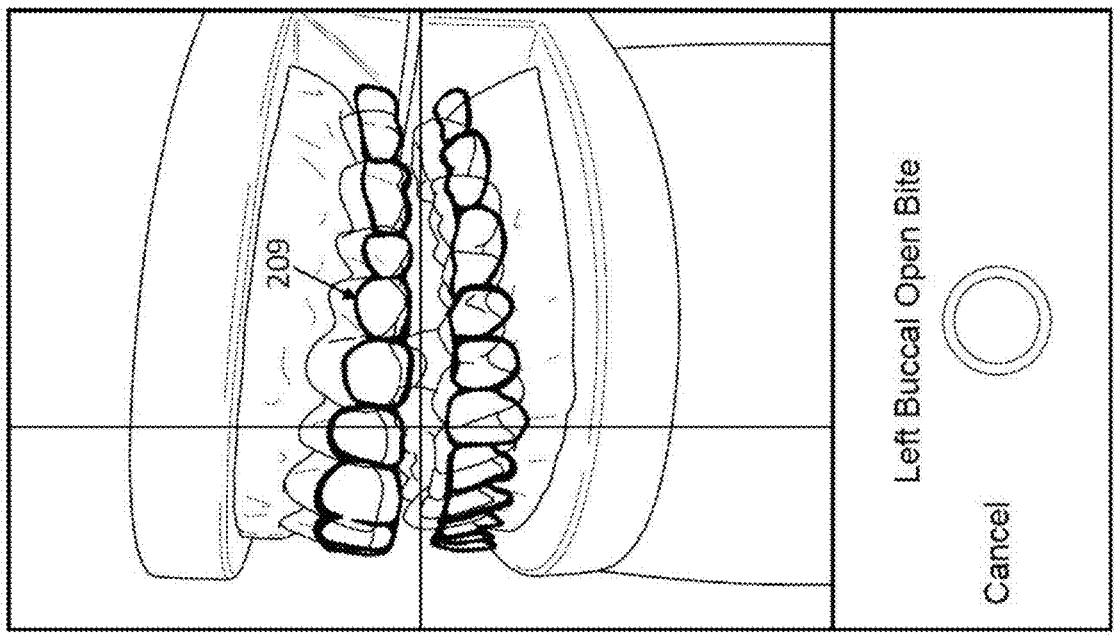

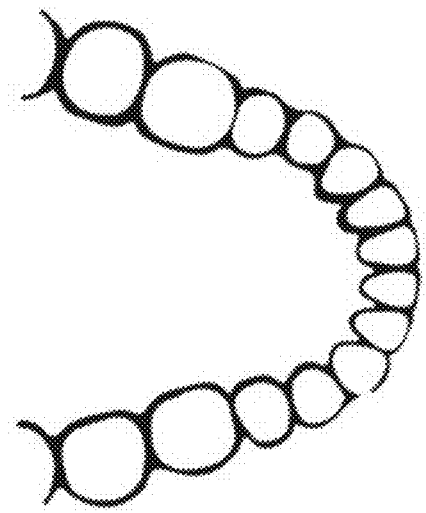
FIG. 4D
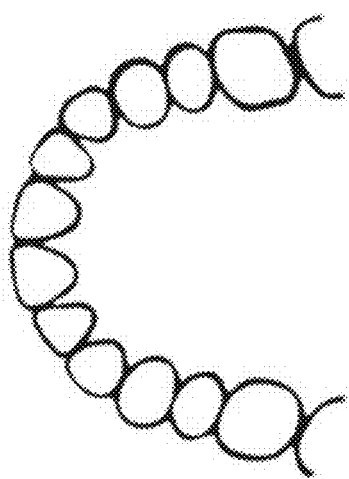
FIG. 4C
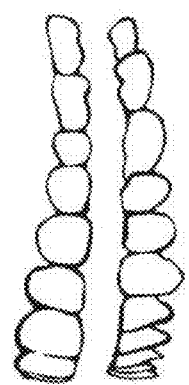
FIG. 4H
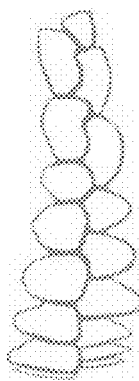
FIG. 4G
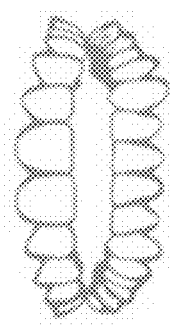
FIG. 4B
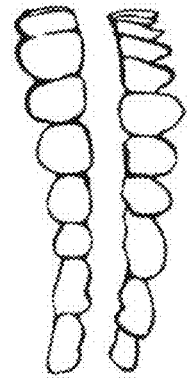
FIG. 4F
FIG. 4E
FIG. 4A Guiding a user, with a mobile telecommunications device, to take a series of images of the patient's teeth in a plurality of predetermined views
851 displaying, on the screen, an overlay comprising an outline of teeth in one of the predetermined views from the plurality of predetermined views, wherein the overlay is displayed atop an image of the patient's teeth 855 capturing the image of the patient's teeth when the overlay approximately matches the patient's teeth in the view of the patient's teeth 857

Transmit the series of images to a remote location to determine if the patient is a candidate for the orthodontic treatment based on the series of images
859

Display, on the screen of the mobile telecommunications device, an indicator that the patient is, or is not, a candidate for the orthodontic treatment
861

FIG. 8B

METHODS AND APPARATUSES FOR DENTAL IMAGES

CLAIM OF PRIORITY

This patent application is a continuation of U.S. patent application Ser. No. 17/543,637, filed Dec. 6, 2021, titled "METHODS AND APPARATUSES FOR DENTAL IMAGES," now U.S. Patent Application Publication No. 2022/0087778, which is a continuation of U.S. patent application Ser. No. 16/952,072, filed Nov. 18, 2020, titled "METHODS AND APPARATUSES FOR DENTAL IMAGES," which is a continuation of U.S. patent application Ser. No. 16/827,594, filed Mar. 23, 2020, titled "METHODS AND APPARATUSES FOR DENTAL IMAGES," now U.S. Pat. No. 10,932,885, which is a continuation of U.S. patent application Ser. No. 15/803,718, filed Nov. 3, 2017, titled "METHODS AND APPARATUSES FOR DENTAL IMAGES," now U.S. Pat. No. 10,595,966, which claims priority to U.S. Provisional Patent Application No. 62/417,985, filed Nov. 4, 2016, and titled "METHODS AND APPARATUSES FOR DENTAL IMAGES," each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

This disclosure relates generally to methods and apparatuses for the analysis of dental images, including methods and apparatuses for capturing dental images and methods and apparatuses for remotely pre-screening a patient for an orthodontic treatment.

BACKGROUND

In dental and/or orthodontic treatment, a set of 2D facial and dental photos is often taken. Traditional dental photography uses a camera, for example, a digital single-lens reflex (SLR) camera with a lens with a focal length of 90-100 mm and circular flash as shown in FIGS. 1A-1C. However, the SLR camera is expensive and it may be difficult to align the teeth of a patient to the SLR camera. The process may also be uncomfortable to the patient. Some doctors and dental technicians may instead attempt to capture dental photos using a mobile phone. However, mobile phones typically have a wide angle camera lens. If a camera of a mobile phone is held sufficiently close to the teeth of the patient to provide an image of the teeth having a high level of detail, dental photos may be blurry and have optical distortion. If the camera of the mobile phone is too far to the teeth, dental photos cannot meet the orthodontic standards. In general, commonly available cameras, and particularly mobile phone cameras, may be faster and easier to use.

Thus, there is a need for new and useful methods and apparatuses for obtaining high quality dental images.

SUMMARY OF THE DISCLOSURE

Described herein are methods, apparatuses (including devices and systems, such as non-transitory, computer-readable storage media and systems including these) for capturing dental images and for using these dental images to determine if a patient is a candidate for an orthodontic procedure. In general, the methods and apparatuses described herein may obtain an image of a patient's teeth for therapeutic use, which may include viewing the patient's teeth, for example, on a screen of a mobile telecommunications device (such as a mobile phone or other hand-held personal computing device, e.g., smartwatch, pad, laptop, etc.).

Any of the methods described herein may include guiding or assisting in taking a predetermined set of images of the patient's teeth from specified viewing angles. The specified viewing angles (views) may be used to manually or automatically determine if a patient is a candidate for a particular orthodontic treatment. Often, it may be necessary or helpful that the views are taken with the proper resolution and focus, particularly when automatically analyzing the images later. Thus, in any of the methods and apparatuses described herein, an overlay may be shown over a camera image while preparing to take a picture of the teeth. The overlay may guide the user (e.g., dental technician, including dentist, orthodontist, dental assistant, nurse, etc.) in taking the images. Further, the overlay may be used to aid in focusing and illuminating the teeth during collection of the images. For example, the methods described herein may include displaying, on a screen (e.g., of a mobile communications device such as a smartphone, etc.), an overlay comprising an outline of teeth in a predetermined view. The overlay may be displayed atop the view from the camera, which may showing a real-time display of from the camera. As the camera is used to image the patient's teeth, the mobile communications device may be moved so that the overlay approximately matches the patient's teeth in the view of the patient's teeth. The method can further comprise capturing an image of the view of the patient's teeth.

For example, a method of obtaining an image of a patient's teeth for therapeutic use is described herein. The method can comprise viewing the patient's teeth, for example, on a screen of a mobile telecommunications device having a camera (e.g., smartphone, mobile phone, etc.). The method can further comprise displaying, on the screen, an overlay comprising an outline of teeth in a predetermined view, wherein the overlay is displayed atop the view of the patient's teeth. The method can comprise moving the mobile telecommunications device relative to the patient's teeth and triggering an indicator when the overlay approximately matches with the patient's teeth. The method can comprise capturing an image of the view of the patient's teeth when the indicator is triggered.

A method to obtain and an image of a patient's teeth for therapeutic use may include viewing, on a screen of a mobile telecommunications device, the patient's teeth. The method can further comprise displaying, on the screen, an overlay comprising a cropping frame and an outline of teeth in one of an anterior view, a buccal view an upper jaw view, or a lower jaw view, wherein the overlay is displayed atop the view of the patient's teeth. The method can further comprise moving the mobile telecommunications device so that the overlay approximately matches the patient's teeth in the view of the patient's teeth. The method can comprise capturing an image of the view of the patient's teeth. The method can further comprise reviewing the captured image on the mobile telecommunications device and indicating on the screen of the mobile telecommunications device if the captured image is out of focus. The method can further comprise automatically cropping the captured image as indicated by the cropping frame.

For example, the overlay can comprise a generic overlay in some embodiments. For another example, the overlay can comprise a patient-specific overlay derived from the patient's teeth in some other embodiments.

For example, the method can further comprise automatically triggering an indicator when the overlay approximately matches with the patient's teeth. For example, the method can further comprise triggering the indicator when the overlay approximately matches with the patient's teeth comprises estimating an indicator of the distance between an edge of the patient's teeth in the view of the patient's teeth and the outline of teeth in the overlay. For another example, the method can further comprise triggering the indicator when the overlay approximately matches with the patient's teeth comprises estimating an indicator of the distance between an edge of the patient's teeth at two or more regions and the outline of teeth and comparing that indicator to a threshold value. For example, the indicator can be a visual indicator, such as a change of color. In some variations, the indicator can be other forms of indicators, such as a voice indicator.

The method can further comprise automatically capturing an image of the patient's teeth when the overlay approximately matches with the patient's teeth.

The method can further comprise checking the image quality of the captured image and displaying on the screen if the image quality is below a threshold for image quality.

The method can further comprise cropping the captured image based on a cropping outline displayed as part of the overlay. Cropping may be manual or automatic.

Any of these methods can further comprise evaluating the captured image for medical treatment by using the image. For example, the method can further comprise transmitting the captured image to a remote server.

The predetermined view can comprise an anterior view, a buccal view an upper jaw view, or a lower jaw view. The predetermined view can comprise a set of dental images according to the orthodontic standards. For example, the method can further comprise repeating the steps of viewing, displaying, moving and capturing to capture anterior, buccal, upper jaw and lower jaw images of the patient's teeth.

The method can further comprise imaging a patient's identification using the mobile telecommunications device and automatically populating a form with user identification information based on the imaged identification.

Any of these methods can further comprise displaying instructions about positioning the patient's teeth on the screen of the mobile telecommunications device prior to displaying the overlay.

Also described herein are apparatuses adapted to perform any of the methods described herein, including in particular software, firmware, and/or hardware adapted to perform one or more of these methods. Specifically, described herein are non-transitory, computer-readable storage media storing a set of instructions capable of being executed by a processor (e.g., of a mobile telecommunications device), that, when executed by the processor, causes the processor to display real-time images of the patient's teeth on a screen of the mobile telecommunications device, display an overlay comprising an outline of teeth in a predetermined view atop the images of the patient's teeth, and enable capturing of an image of the patient's teeth.

For example, described herein are non-transitory, computer-readable storage media storing a set of instructions capable of being executed by a processor of a mobile telecommunications device, that, when executed by the processor, causes the processor to display real-time images of the patient's teeth on a screen of the mobile telecommunications device, display an overlay comprising an outline of teeth in a predetermined view atop the images of the patient's teeth, trigger an indicator when the overlay approximately matches with the patient's teeth, and enable capturing of an image of the patient's teeth when the indicator is triggered.

Also described herein are non-transitory, computer-readable storage medium storing a set of instructions capable of being executed by a processor of a mobile telecommunications device, that, when executed by the processor, causes the processor to display real-time images of the patient's teeth on a screen of the mobile telecommunications device and display an overlay comprising a cropping frame and an outline of teeth in one of an anterior view, a buccal view an upper jaw view, or a lower jaw view, wherein the overlay is displayed atop the images of the patient's teeth, and enable capturing of an image of the patient's teeth. The non-transitory, computer-readable storage medium, wherein the set of instructions, when executed by the processor, can further cause the processor to review the captured image and indicate on the screen if the captured image is out of focus and automatically crop the captured image as indicated by the cropping frame.

The set of instructions, when executed by the processor, can further cause the processor to display a generic overlay. For another example, set of instructions can cause the processor to display a patient-specific overlay derived from the patient's teeth.

The set of instructions, when executed by the processor, can further cause the processor to automatically trigger an indicator when the overlay approximately matches with the patient's teeth. For example, the set of instructions can further cause the processor to estimate an indicator of the distance between an edge of the patient's teeth in the view of the patient's teeth and to trigger the indicator when the outline of teeth in the overlay is less than or equal to a threshold value. The set of instructions, when executed by the processor, can further cause the processor to estimate an indicator of the distance between an edge of the patient's teeth at two or more regions in the view of the patient's teeth and to trigger the indicator when the outline of teeth in the overlay is less than or equal to a threshold value. The set of instructions can cause the processor to trigger the indicator by displaying a visual indicator on the screen. Any appropriate visual indicator may be displayed, including a color, intensity (e.g., changing the color and/or intensity of the outline of the teeth overlay, cropping window, etc.), a textual/character indicator, or some combination thereof. Alternatively or additionally the indicator may be audible (beeping, tonal, etc.) and/or tactile (a vibration, buzzing, etc.).

The set of instructions, when executed by the processor, can further cause the processor to check the image quality of the captured image and displaying on the screen if the image quality is below a threshold for image quality. The quality may automatically determine focus, lighting (dark/light), etc. of the image and may alert the user and/or automatically reject or accept the image. The apparatus may further process the image (e.g., sharpen, lighten/darken, etc., including cropping). For example, the non-transitory, computer-readable storage medium, wherein the set of instructions, when executed by the processor, can further cause the processor to automatically crop the captured image based on a cropping outline displayed as part of the overlay.

The set of instructions, when executed by the processor, can further cause the processor to transmit the captured image to a remote server. Transmission may be automatic or manual.

The apparatus (e.g., including the non-transient set of instructions) can further cause the processor to display an overlay comprising an outline of teeth in a predetermined view such as an anterior view, a buccal view an upper jaw view, or a lower jaw view. The apparatus may be configured to take a full or partial set of views. For example, the set of instructions, when executed by the processor, can further cause the processor to repeat the steps of viewing, displaying, moving and capturing to capture anterior, buccal, upper jaw and lower jaw images of the patient's teeth.

In addition to taking one or more views (e.g., anterior, buccal, upper jaw and lower jaw) the apparatuses described herein may be configured to automatically determine patient-specific information on the identity and other patient characteristics, and to associate this information with the images taken. For example, the set of instructions can cause the processor to capture an image of a patient's identification (e.g., driver's license) using the mobile telecommunications device and automatically populate a form with user identification information based on the imaged identification.

In any of these apparatuses the set of instructions can further cause the processor to display instructions on positioning the patient's teeth on the screen of the mobile telecommunications device prior to displaying the overlay.

Any of the methods described herein may be methods to obtain a series of images of a patient's teeth. These methods may include: displaying, on a screen of a mobile telecommunications device having a camera, a real-time image from the camera; and guiding a user in taking a series of predetermined views of the patient's teeth by sequentially, for each predetermined view: displaying, superimposed over the real-time image on the screen, an overlay comprising an outline of teeth in a predetermined view from the plurality of predetermined views; and triggering the capture of an image of the patient's teeth when the overlay approximately matches with the image of the patient's teeth in the display on the screen.

For example, a method to obtain a series of images of a patient's teeth may include: displaying, on a screen of a mobile telecommunications device having a camera, the patient's teeth; and guiding a user in taking a series of predetermined views of the patient's teeth by sequentially, for each predetermined view: displaying, on the screen, an overlay comprising an outline of teeth in a predetermined view, wherein the overlay is displayed atop the view of the patient's teeth; automatically adjusting the camera to focus within a region of the screen that is within the overlay; automatically adjusting a light emitted by the camera based on a level of light of within the region of the screen that is within the overlay; and triggering the capture of an image of the patient's teeth when the overlay approximately matches with the patient's teeth in the display of the patient's teeth, wherein the predetermined views include at least one each of: an anterior view, a buccal view, an upper jaw view, and a lower jaw view.

A series of images of a patient's teeth may include a set, collection, or grouping. A series may be organized or ordered, e.g., in a predefined order based on the predefined views (e.g., viewing angles). The series of images may be collected or linked to together, and may include identifying information, including information identifying the corresponding viewing angle (e.g., anterior view, buccal view, an upper jaw view, a lower jaw view, etc.). In any of these variations additional information may be included, such as the user and/or patient's chief dental concern (e.g., crowding, spacing, smile width, arch width, smile line, horizontal overjet, vertical overbite, cross bite, bite relationship, etc.). In general, the set of images may refer to a series of predetermined views. The predetermined views may refer to predetermined viewing angles for visualizing the teeth. Viewing angles may refer to the view of the upper and/or lower dental arch, and may include, for example: anterior (e.g., upper and lower anterior, typically with a closed bite), anterior open bite, right buccal (typically with a closed bite), right buccal open bite, left buccal (typically with a closed bite), left buccal open bite, upper jaw (e.g., viewed from occlusal surface), and lower jaw (e.g., viewed from an occlusal surface). The predetermined views may also include views that include the entire head, e.g., a head profile, a facial view (typically with the mouth closed, unsmiling), as well as a facial view with the patient smiling. A dental mirror may be used to take the upper and lower jaw images. The systems and methods described herein may automatically determine if a mirror is used, and may orient the image accordingly.

Any of the methods and apparatuses described herein may guide a user in taking a series. The method or apparatus may provide audible and/or visual instructions to the user. In particular, as mentioned above, any of these apparatuses may include an overlay on the display (screen) of the mobile telecommunications device showing an outline that may be matched to guide the user in taking the image(s). The overlay may be shown as an outline in a solid and/or semi-transparent color. An overlay may be shown for each predetermined view. The user may observe the screen and, once the image shows the patient's anatomy approximately matching within the overlay, the image may be captured. Image capture may be manual (e.g., manually triggered for capture by the user activating a control, such as pushing a button to take the image) and/or automatic (e.g., detected by the system and automatically triggered to take the image when the overlay is matched with the corresponding patient anatomy). In general, capturing or triggering the capture of the image of the patient's teeth (and/or the patient's head) when the overlay approximately matches with the image of the patient's teeth in the display may refer to automatic capturing/automatic triggering, semi-automatic capturing/semi-automatic triggering, or manual capturing/manual triggering. Automatic triggering (e.g., automatic capturing) may refer to automatic capture of the image, e.g., taking one or more images when the patient's anatomy (e.g., teeth) show on the screen matches the overlay on the screen. Semi-automatic triggering (e.g., semi-automatic capturing) may refer to producing a signal, such as an audible sound and/or visual indicator (e.g., flashing, color change, etc.) when the patient's anatomy (e.g., teeth) shown on the screen matches the overlay on the screen. Manual triggering (e.g., manual capturing) may refer to the user manually taking the image, e.g., taking one or more images when the patient's anatomy (e.g., teeth) is shown on the screen to match the overlay.

As described in greater detail herein, automatic or semi-automatic triggering (e.g., automatic or semi-automatic capture of images) may be accomplished by a variety of well-known image processing techniques. For example, detection of a match between the patient's anatomy (e.g., teeth) and the overlay on a screen may be achieved by edge detection; the edge of the patient's teeth may be compared to the overly region and if two or more regions (e.g., two opposite regions, etc.) are within a defined distance (e.g., +/−1 mm, +/−2 mm, +/−3 mm, +/−4 mm, +/−5 mm, +/−6 mm, +/−7 mm, +/−8 mm, +/−10 mm, etc. or +/−a corresponding number of pixels for the image, +/−a percentage, such as 1%, 2%, 3%, 5%, 7%, 10%, etc. of the screen diameter, etc.). The automatic detection of match may be determined by machine learning, e.g., training a machine to recognize matching of the patient anatomy (e.g., teeth) within the overlay with an acceptable percentage of match.

Any of these methods may include displaying on a screen of the mobile telecommunications device, images, and particularly real-time images, from the camera of the mobile telecommunications device. Real-time may be refer to the current, or approximately concurrent, display of images detected by the camera on a screen or screens, e.g., of the mobile telecommunications device.

In general, the overlay may also be used to improve the image quality. Of the image(s) being taken. For example, any of these methods and apparatuses may automatically focus the imaging only within the region defined by the overlay. For example, any of these methods and apparatuses may disable or modify the autofocusing of the camera of the mobile telecommunications device (e.g., mobile phone) and may autofocus on just the region within the overlay, or a sub-region within the overlay (e.g., on the anterior teeth, the incisor, canine, bicuspid, molars, etc.).

The overly may also control the illumination (e.g., lighting) of the images based on the region within all or a portion of the overlay. For example, the apparatus or method may detect and adjust the light level based on the light level within the overlay or a sub-region within the overlay (e.g., on the incisors, canines, bicuspids, molars, etc.). The illumination may generally be provided by the mobile telecommunications device, which may include a flash or LED light source that can be adjusted for continuous and/or discrete illumination.

In any of the methods and apparatuses described herein, the images taken for particular views (e.g., anterior, anterior open bite, right buccal, right buccal open bite, left buccal, left buccal open bite, upper jaw, and lower jaw, etc.) may be labeled with the corresponding view, either manually or automatically. Further, the view may be detected and identified by the method or apparatus. In variations in which the overlay for a particular view is provided before taking the image, the view shown in the overlay may determine the label for the resulting image. As mentioned herein, in some variations, automatic detection of the nearest view may be performed on the imaging, and the view (viewing angle) may be detected automatically. Additionally or alternatively, mirror images, may be detected or identified, and the resulting images flipped/rotated, and/or labeled to indicate that a dental mirror was used to take the image.

In any of the methods and apparatuses described herein, the overlay displayed over an image on the screen of the mobile telecommunication device may be selected automatically, e.g., by identifying the closest match to one of the predetermined viewing angles. The overly having the closet match may then be used to take an image for the set of images. Alternatively or additionally, the overlay may be provided first, and the user may then move the camera portion of the mobile telecommunications device to fit the patient's anatomy into the overlay.

As mentioned, any of the images for predetermined viewing angles (views) described herein may be taken with the use of a cheek retainer. An apparatus instruction the user to take the images may include written, pictorial (visual) and/or audible instruction on the use of the cheek retainer. Any of the methods and apparatuses described herein may automatically detect a cheek retainer; this may aid in automatic labeling and interpretation of the resulting image(s). In some variations the apparatus and/or method may detect one or more markers on the cheek retainer and use this information identify a view, to identify a match between an image and an overlay, etc.

Also described herein are methods and apparatuses for remotely pre-screening a patient for an orthodontic treatment. Any orthodontic treatment may be attempted, particularly orthodontic treatments for aligning the patient's teeth. Typically such methods may include taking a series of predetermined views of the patient's teeth, and optionally collecting information about the patient, such as one or more chief dental concerns (e.g., a chief patient dental concern such as, e.g., crowding, spacing, smile width, arch width, smile line, horizontal overjet, vertical overbite, cross bite, bite relationship, etc.). This additional information may be linked to the series of images, and may be used, along with the series of images, to determine if a patient is, or is not, a good candidate for an orthodontic treatment.

For example, described herein are methods for remotely pre-screening a patient for an orthodontic treatment, the method comprising: guiding a user, with a mobile telecommunications device having a camera, to take a series of images of the patient's teeth in a plurality of predetermined views; transmitting the series of images from the mobile telecommunications device to a remote location to determine if the patient is, or is not, a candidate for the orthodontic treatment based on the series of images; and displaying, on a screen of the mobile telecommunications device, an indicator that the patient is, or is not, a candidate for the orthodontic treatment.

In any of these methods, guiding may refer to sequentially, for each predetermined view, displaying, on the screen, an overlay comprising an outline of teeth in one of the predetermined views from the plurality of predetermined views, wherein the overlay is displayed atop an image of the patient's teeth. The overlay may be provided first, or the overlay may be selected from the set of overlay viewing angles that best matches the current view being imaged by the mobile telecommunications device. Alternatively, the predetermined views may be presented in a fixed order.

As mentioned, guiding the user may include, for each predetermined view, capturing an image of the patient's teeth when the image of the patient's teeth approximately matches an overlay corresponding to a predetermined view. Capturing may be manual, automatic or semi-automatic, as discussed above. For example, any of these methods may include automatically determining when the image of the patient's teeth approximately matches the overlay by detecting an edge of the patient's teeth and comparing the detected edge to the overlay.

Any of these methods and apparatuses may include automatically adjusting the camera to focus the camera within a region of the screen that is within the overlay. This region may include all of the region within the overlay, or a sub-set (e.g., corresponding to the anterior teeth, the posterior teeth, etc.

Any of these methods and apparatuses may include selecting the overlay based on one or more images of the patient's teeth. This may include selecting the overlay corresponding to the particular viewing angle, as mentioned above, and/or it may include customizing the overlay based on the patient's specific anatomy. For example the overlay maybe selected to match the shape, size and arrangement of the patient's dentition.

Any of these methods and apparatuses may include automatically adjusting the light emitted by the camera based on a level of light of within a region of the screen that is within the overlay. The light may be continuous or intermittent (e.g., flash). Thus, the apparatus or method may first disable the default light sensing for the mobile telecommunications device, and may instead use the region (or a sub-section of the region) within the overlay to set the light level for adjusting the flash/applied light from the mobile telecommunications device.

As mentioned, any of these methods and apparatuses may be configured to capture the image of the patient's teeth when the image of the patient's teeth approximately matches the overlay corresponding to the predetermined view, e.g., by automatically capturing the image. Similarly, any of these methods and apparatuses may capture the image of the patient's teeth when the image of the patient's teeth approximately matches the overlay corresponding to the predetermined view by semi-automatically capturing, e.g., triggering a visual, audible, or visual and audible indicator that permits the user to take the image. In some variations a plurality of images may be taken and averaged or used to select the best image.

Transmitting the series of images from the mobile telecommunications device to the remote location may generally include receiving, in the mobile telecommunications device, an indication that patient is, or is not, a candidate within a fixed period of time (e.g., 10 minutes, 15 minutes, 20 minutes, etc.) from transmitting the series of images. In general, the initial decision that a patient is a good candidate for the orthodontic treatment may use the set of images transmitted, and may also include the chief concern. The decision may be made at the remote location (e.g., a remote server, etc.) either manually or automatically. Automatic decisions may be based on the amount of movement required to position the teeth in order to or address the chief concern and/or a standard of orthodontic positioning. The methods and apparatuses describe herein may provide images with sufficient clarity so that individual tooth positions may be determined relative to the dental arch and used to at least roughly approximate the complexity of an orthodontic procedure. Cases in which the amount and/or type of movement is complex may be indicated as not candidates. Cases in which the amount and/or type of movement is not complex may be indicated as candidates. Complex dental movements may include movements of greater than a minimum threshold (e.g., greater than 3 mm distal/proximal movement, greater than 4 mm distal/proximal movement, 5 mm distal/proximal movement, greater than 6 mm distal/proximal movement, greater than 7 mm distal/proximal movement, etc.), and/or rotation of greater than a minimum threshold (e.g., greater than 5, 10, 15, 20, 25, 30, 35, 45, etc., degrees), and/or extruding of one or more teeth greater than a minimum threshold (e.g., greater than 0.5 mm, 1 mm, 2 mm, 3 mm, 4 mm, etc.).

As mentioned, in general, any of these methods and apparatuses may include automatically identifying each image of the series of images to indicate which view of the plurality of views each image includes (e.g., anterior, anterior open bite, right buccal, right buccal open bite, left buccal, left buccal open bite, upper jaw, lower jaw, etc.). Any of these methods may also include automatically determining if one or more of the series of images was taken using a mirror. For example, the image may be automatically examined to identify reflections (e.g., a plane or mirror), and/or to determine if the orientation of the teeth within the image are reversed (mirrored) in the image. Mirrored images may be reversed for display as a non-mirrored image. Alternatively or additionally, duplicate mirrored regions may be cropped from the image.

Any of the methods and apparatuses described herein may include receiving, in the mobile telecommunications device, an indication of the patient's chief dental concern and aggregating the patient's chief dental concern with the series of images. Transmitting the series of images may comprise transmitting the aggregated series of images and the patient's chief dental concern.

As mentioned, any of the methods and apparatuses described herein may be configured to include instructing the user to retract the patient's cheek with a cheek retractor. A marker on the cheek retractor may be used to automatically identify the image to indicate which view of the plurality of views it includes based on the identified cheek retractor.

Although the terms "user" and "patient" are used separately herein, the user may be the patient. For example, the person taking the images using the methods and apparatuses described herein may be the patient. Thus, in any of these methods, the user may be the patient. Alternatively, a separate use (e.g., dentist, orthodontist, dental technician, dental assistant, etc.) may act as the user, taking the images as described herein on a patient.

A method for remotely pre-screening a patient for an orthodontic treatment may include: guiding a user, with a mobile telecommunications device having a camera, to take a series of images of the patient's teeth in a plurality of predetermined views by sequentially, for each predetermined view: displaying, on the screen, an overlay comprising an outline of teeth in one of the predetermined views from the plurality of predetermined views, wherein the overlay is displayed atop an image of the patient's teeth; and capturing the image of the patient's teeth when the overlay approximately matches the patient's teeth in the view of the patient's teeth; transmitting the series of images to a remote location to determine if the patient is a candidate for the orthodontic treatment based on the series of images; and displaying, on the screen of the mobile telecommunications device, an indicator that the patient is, or is not, a candidate for the orthodontic treatment.

A method for remotely pre-screening a patient for an orthodontic treatment may include: guiding a user, with a mobile telecommunications device having a camera, to take a series of images of the patient's teeth from a plurality of predetermined views by sequentially displaying, on a screen of the mobile telecommunications device, an overlay comprising an outline of teeth in each of the predetermined views; receiving, in the mobile telecommunications device, an indication of the patient's chief dental concern; aggregating, in the mobile telecommunications device, the series of images and the chief dental concern; transmitting the aggregated series of images and the chief dental concern to a remote location to determine if the patient is a candidate for the orthodontic treatment based on the series of images; and displaying, on the screen of the mobile telecommunications device, an indicator that the patient is, or is not, a candidate for the orthodontic treatment.

Any of the methods (and method steps) described herein may be performed by an apparatus configured to perform the method(s). For example, described herein are systems for remotely pre-screening a patient for an orthodontic treatment. A system for remotely pre-screening a patient (e.g., remote to the patient) may include: a non-transitory, computer-readable storage medium storing a set of instructions capable of being executed by a processor of a mobile telecommunications device having a camera, that, when executed by the processor, causes the processor to: guide a user to take a series of images of the patient's teeth in a plurality of predetermined views with the camera; transmit the series of images from the mobile telecommunications device to a remote location to determine if the patient is a candidate for the orthodontic treatment based on the series of images; and display, on a screen of the mobile telecommunications device, an indicator that the patient is, or is not, a candidate for the orthodontic treatment. The non-transitory, computer readable storage medium may cause the processor to guide the user to take the series of images of the patient's teeth by: displaying, on the screen of the mobile telecommunications device, an image from the camera and an overlay comprising an outline of teeth in one of the predetermined views from the plurality of predetermined views, wherein the overlay is displayed atop the image from the camera. The non-transitory, computer readable storage medium may cause the processor to guide the user to take the series of images of the patient's teeth by automatically adjusting the camera to focus the camera within a region of the screen that is within the overlay. The non-transitory, computer readable storage medium may causes the processor to guide the user to take the series of images of the patient's teeth by selecting the overlay based on one or more images of the patient's teeth. The non-transitory, computer readable storage medium may cause the processor to guide the user to take the series of images of the patient's teeth by automatically adjusting a light emitted by the camera based on a level of light of within a region of the screen that is within the overlay.

The non-transitory, computer readable storage medium may cause the processor to guide the user to take the series of images of the patient's teeth by: indicating when an overlay comprising an outline of teeth in one of the predetermined views from the plurality of predetermined views aligns with a view of the patient's teeth from the camera, wherein the overlay is displayed atop the view from the camera. The non-transitory, computer readable storage medium may cause the processor to guide the user to take the series of images of the patient's teeth by: automatically taking an image of the patient's teeth when an overlay comprising an outline of teeth in one of the predetermined views from the plurality of predetermined views aligns with a view of the patient's teeth from the camera, wherein the overlay is displayed atop the view from the camera.

The non-transitory, computer readable storage medium may cause the processor to guide the user to take the series of images of the patient's teeth comprises guiding the user to take at least one each of: an anterior view, a buccal view, an upper jaw view, and a lower jaw view.

Any of these systems may be configured so that the non-transitory, computer readable storage medium further causes the processor to receive, in the mobile telecommunications device, an indication that patient is, or is not, a candidate within 15 minutes of transmitting the series of images. The non-transitory, computer readable storage medium may cause the processor to automatically identify each image of the series of images to indicate which view of the plurality of views each image includes. The non-transitory, computer readable storage medium may cause the processor to automatically determine if one or more of the series of image was taken using a mirror.

The non-transitory, computer readable storage medium may further cause the processor to receive, in the mobile telecommunications device, an indication of the patient's chief dental concern and aggregating the patient's chief dental concern with the series of images, further wherein the non-transitory, computer readable storage medium may be configured to transmit the series of images as the aggregated series of images and the patient's chief dental concern.

The non-transitory, computer readable storage medium may further cause the processor to instruct the user to retract the patient's cheek with a cheek retractor, and/or to identify a marker on the cheek retractor and to mark an image from the plurality of predetermined views to indicate which view of the plurality of views it includes based on the identified cheek retractor.

Any of the systems described herein may include a remote processor configured to receive the transmitted series of images and to transmit an indicator that the patient is, or is not, a candidate for the orthodontic treatment based on the series of images back to the non-transitory, computer-readable storage medium.

For example, a system for remotely pre-screening a patient for an orthodontic treatment may include a non-transitory, computer-readable storage medium storing a set of instructions capable of being executed by a processor of a mobile telecommunications device having a camera, that, when executed by the processor, causes the processor to: guide a user to take a series of images of the patient's teeth in a plurality of predetermined views by sequentially, for each predetermined view: displaying, on a screen of the mobile telecommunications device, an image from the camera and an overlay comprising an outline of teeth in one of the predetermined views from the plurality of predetermined views, wherein the overlay is displayed atop the image from the camera; and capturing the image when the overlay approximately matches the patient's teeth on the screen; and transmit the series of images to a remote location.

A system for remotely pre-screening a patient for an orthodontic treatment may include: a non-transitory, computer-readable storage medium storing a set of instructions capable of being executed by a processor of a mobile telecommunications device having a camera, that, when executed by the processor, causes the processor to: guide a user to take a series of images of the patient's teeth in a plurality of predetermined views by sequentially, for each predetermined view: displaying, on a screen of the mobile telecommunications device, an image from the camera and an overlay comprising an outline of teeth in one of the predetermined views from the plurality of predetermined views, wherein the overlay is displayed atop the image from the camera; and capturing the image when the overlay approximately matches the patient's teeth on the screen; and transmit the series of images to a remote location; and a remote processor configured to receive the transmitted series of images and to transmit an indicator that the patient is, or is not, a candidate for the orthodontic treatment based on the series of images back to the non-transitory, computer-readable storage medium.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 1A shows an example of a traditional SLR camera taking an anterior open bite view of a patient's teeth. FIG. 1B shows an anterior view (closed bit) taken with the traditional SLR camera, using a pair of cheek retractors that the patient holds onto, as shown in FIG. 1C.

FIG. 2A illustrates an example of a screen of an apparatus (such as a system configured to perform the method as described herein) including an overlay comprising an outline of teeth in a predetermined view, shown as an anterior view of teeth, on a screen of a mobile telecommunications device.

FIG. 2B illustrates another example of an example of the screen of the apparatus, similar to that shown in FIG. 2B, showing the overlay and another anterior view of teeth. For purposes of illustration the model is shown as a dental model (e.g., positive cast) of a patient's dentition; the teeth may be directly imaged, either with or without a retractor.

FIG. 2C shows an example of a screen of an apparatus configured to take images (e.g., photographs) of a patient's teeth in a left buccal open bite configuration, including an overlay on the screen which shows what teeth should be visible in the view.

FIGS. 4A-4H illustrate 8 specific overlay images for the required types of photos according to the orthodontic standard, including an anterior view in FIG. 4A, an another anterior view in FIG. 4B, an upper jaw view in FIG. 4C, a lower jaw view in FIG. 4D, a left buccal view in FIG. 4E, an another left buccal view in FIG. 4F, a right buccal view in FIG. 4G, and an another right buccal view in FIG. 4H.

FIG. 8B is an example of a method of remotely pre-screening a patient for an orthodontic treatment using the method of FIG. 8A.

in FIG. 12B the focus is on the lips and gingiva, while in FIG. 12C, the focus is on the teeth, which will appear more in-focus compared to FIG. 12B.

In FIGS. 13A and 13B, the line drawings are adapted from photographs showing images taken without and with, respectively, the lighting being adjusted based on the overlay region.

In FIG. 14C the retractor includes one or more markers that may be used to identify the position of the retractor (and therefore the patient's teeth) relative to the view.

In FIG. 15, the patient is positioned a distance from the camera, and the methods and apparatuses described herein may indicate that the camera should be moved closer.

DETAILED DESCRIPTION

The following description of the various embodiments of the invention is not intended to limit the invention to these embodiments, but rather to enable any person skilled in the art to make and use this invention.

Described herein are methods and apparatuses (including devices, systems, non-transitory, computer-readable storage medium storing instructions capable of being executed by a processor, etc.) for capturing high quality dental images, including obtaining an image or set of images at predetermined positions of a patient's teeth and/or face for therapeutic use. In particular, described herein are methods and apparatuses for remotely pre-screening a patient for an orthodontic treatment that includes taking a defined set of images of the patient's teeth at known angles, and transmitting them as a set for remote analysis. The images must be at the predetermined angles and must be sufficiently well focused and illuminated, as will be described herein, despite being taken with the built-in camera found in most mobile telecommunications devices. The methods (and apparatuses for performing them) described herein guide a user in taking the images of the patient's teeth, for example, by displaying an overlay comprising an outline of teeth in a predetermined view (or sequence of predetermined views), on a screen of a mobile telecommunications device, wherein the overlay is displayed atop the view of the patient's teeth (or other body parts, such as face, head, etc.). The user may then move the mobile telecommunications device so that the overlay approximately matches the patient's teeth in the view of the patient's teeth and capture (e.g., manually or automatically by means of the apparatus) an image of the view of the patient's teeth (and in some instances, face and head).

Figure 1B:
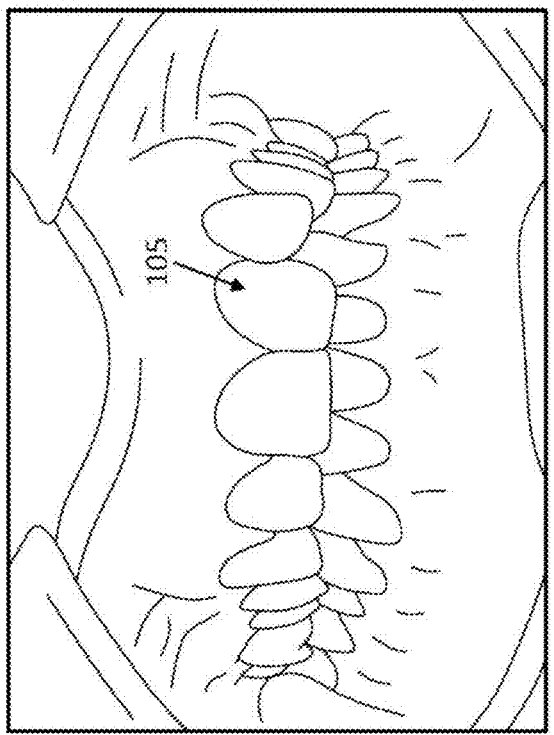
FIGS. 1A-1C illustrate one example of traditional dental photography using a digital SLR camera.
Figure 1C:
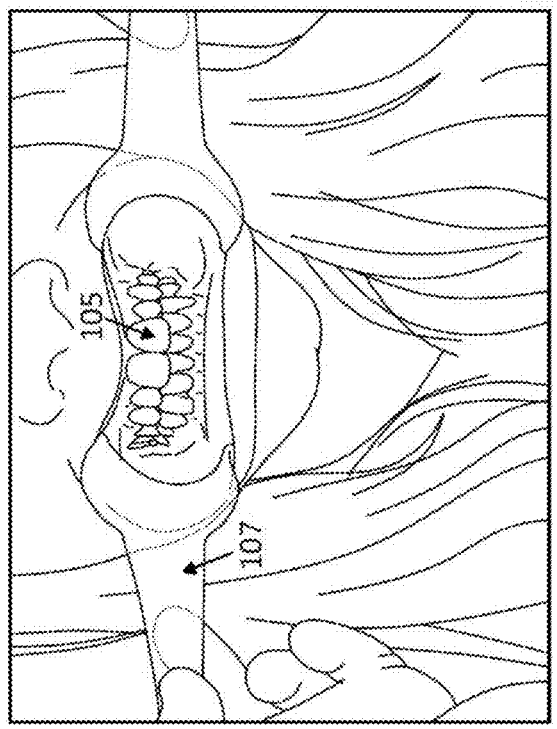
Figure 1A:
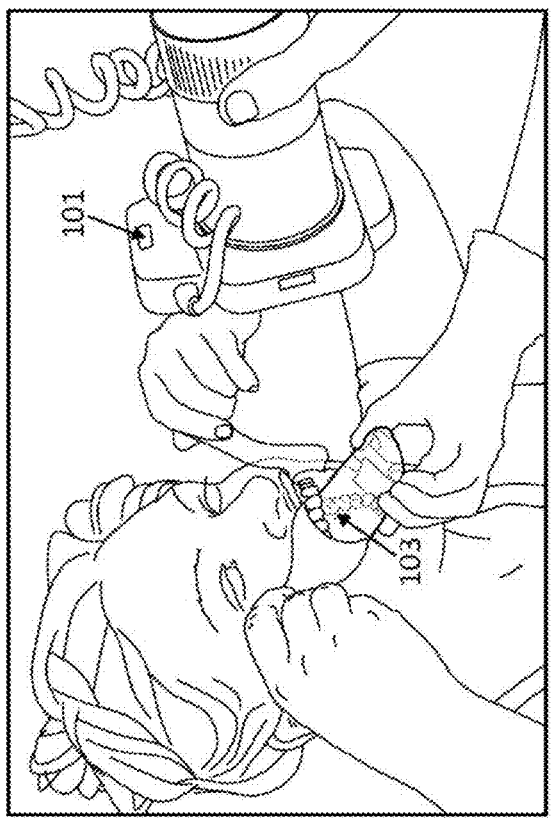

Mobile telecommunications devices can be used to capture dental images instead of using expensive and bulky SLR cameras. FIG. 1A shows the use of a traditional SLR camera 101 to image a patient's teeth 103. The camera is typically held by the user (e.g., dentist, orthodontist, dental technician, etc.) and images are taken of the patient's mouth from various positions. The user must manually adjust the patient position and/or camera position. FIG. 1B shows a typical image of an anterior view 105 of a patient's teeth taken with an SLR camera. In addition, one or more retractors 107 or other elements may be used to assist in taking the photograph, as shown in FIG. 1C. Any of the methods and apparatuses described herein may include the use of one or more such retractors or other assistance devices (including mirrors, probes, etc.), and the apparatuses described herein may prompt the user to place and/or position such devices, including providing guidance for proper positions.

It may be particularly helpful to adapt a traditional handheld consumer electronics device, such as phone (e.g., smartphone, smartwatch, pad, tablet, etc.) to take one or, more preferably, a series of images of the teeth at sufficient clarity, e.g., focus, magnification, resolution, lighting, etc. so that these images may be used to track a patient's progress and/or pre-screen the patient for a dental or orthodontic procedure. Thus, such images (and image series) when taken from the proper orientations and with sufficient clarity (focus, magnification, resolution, lighting, etc.) may be used in one or more of: planning a dental/orthodontist procedure, determining the feasibility of a dental/orthodontic procedure for a particular patient, tracking patient progress during a dental/orthodontic procedure, determining the effectiveness of a dental/orthodontic procedure, etc. For example, and of the methods and apparatuses described herein may be used to specifically track a portion of an orthodontic procedure, including one or more phases of treatment (such as palatal expansion).

In general, these method and apparatuses may improve on existing technology by guiding a user through the process of collecting relevant patient images (e.g., a predetermined set of images), enhancing and/or confirming the image quality, associating patient information and transmitting the set of images so that they may be used in a dental/orthodontic procedure.

For example, the methods and apparatuses described herein may use a user's own handheld electronics apparatus having a camera (e.g., smartphone) and adapt it so that the user's device guides the user in taking high-quality images (e.g., at the correct aspect ratio/sizing, magnification, lighting, focus, etc.) of a predetermined sequence of orientations. In particular, these apparatuses and methods may include the use of an 'overlay' on a real-time image of the screen, providing immediate feedback on each of the desired orientations, which may also be used to adjust the lighting and/or focus, as described herein.

An overlay may include an outline (e.g., a perspective view outline) of a set of teeth that may be used as a guide to assist in placement of the camera to capture the patient image. The overlay may be based on a generic image of teeth, or it may be customized to the user's teeth, or to a patient-specific category (by patient age and/or gender, and/or diagnosis, etc.). The overlay may be shown as partially transparent, or it may be solid, and/or shown in outline.

FIG. 2A illustrates an example of an overlay 201 comprising an outline of teeth in a first predetermined view, shown here as an anterior view of teeth, on a screen 203 of a mobile telecommunications device. FIG. 2B illustrates another example of the overlay 201 in another anterior view of teeth, on the screen 203 of the mobile telecommunications device displaying a real-time camera image (viewing a dental model of a patient's teeth). As shown in FIGS. 2A and 2B, the on-screen overlay is displayed atop the view of the model of the patient's teeth. The on-screen overlay can help guide a user to move the mobile telecommunications device to a desired position such that the overlay matches (or approximately matches, e.g., within 5%, 10%, 15%, 20%, 25%, 30%, etc. of the outer or inner edge of the overlay, or a percentage of the overlay, e.g., >5%, 10%, 15%, 20%, 25%, 30%, etc.) the view of the patient's teeth, in this example, shown as a model of the patient's teeth. Therefore, a user can be guided to take dental photos by the on-screen overlay, saving time and effort. As will be described in greater detail below. The system may be configured to manually, automatically or semi-automatically take the image when the patient's teeth are within the overlay. In FIG. 2A the teeth are shown too far from the camera, and do not line up with the overlay; in FIG. 2B the teeth are too close, though they are near an approximate match.

High quality dental images are usually required to submit a dental case or request a case assessment. The overlay on the screen of the mobile telecommunications device can increase the quality of dental images by increasing the accuracy of the alignment of the camera lenses with teeth of the patient. The on-screen overlay with the outline of teeth can help doctors to take quality dental photos using the mobile telecommunications device.

The dental photos captured by the mobile telecommunications device can be uploaded automatically. In general, the methods described herein can increase the efficiency of the user. Taking dental photos by using the method disclosed herein can be much faster than using digital cameras. The dental images captured by the method can be of a higher quality and consistency than simply using a default camera application of a mobile telecommunications device.

As shown in FIGS. 2A and 2B, users can approximately match visually on-screen overlay with the teeth of the patient. The camera of the mobile telecommunications device has to be positioned at a right distance and a right angle relative to the teeth in order to capture a high quality dental image. The user can refer to the on-screen overlay to guide the movement of the mobile telecommunications device camera to set a correct view and distance to the teeth of the patient in the view of the patient's teeth. The overly can help to precisely align the phone camera lens with the teeth of the patient and position the mobile telecommunications device at a right distance and a right angle to the teeth of the patient. For example, the mobile telecommunications device may have to be placed close enough to the teeth without being too close. Matching the overlay with the teeth of the patient can greatly facilitate the process of alignment. Once the overlay is matching (and the image focused, e.g., using autofocusing, and particularly autofocusing within all or a portion of the overly, as described below), the image of the view of the patient's teeth can be captured.

The overlay with an outline of teeth in a predetermined view can further provide information such as required visible teeth in the predetermined view. For example, FIG. 2C, illustrates a buccal view overlay 209 which shows what teeth should be visible in the view. In this example, the overlay may be based on actual patient teeth, or may be generated from a typical patient or synthesized from a population of patients to form an average or typical overlay arrangement. In general, an approximate visual match is needed to select the correct distance, correct angle and correct view of the patient's teeth. Also described herein are overlays that are based on the patient's approximate dentition. In some variations the overlay may be progressively refined as the patient's teeth is imaged, so that an increasingly accurate match between the overlay and the patient's teeth may be made. For example, as an image is focused, and/or as the camera is brought closer to the patient's teeth, the overlay may be refined to better match the patient's teeth. In some cases a generic patient overlay may not match the patient's teeth even when aligned (e.g., if the patient has gaps or spacing in the teeth, etc.). Thus, the method or apparatus may start with a generic overlay and may thereafter refine the overlay in a manner that is specific to the patient's teeth. For example, as mentioned herein, the system may be trained to recognize or categorize the teeth and select an appropriate overlay, or accept an existing overlay as sufficient.

An overlay can be an average (generic) overlay obtained by an artificial model. The average overlay may not require specific information from a patient. For example, the average overlay can be obtained from an artificial model which approximately fits most of patients. Users can be guided to approximately match the average overlay with the teeth of a patient. In some other embodiments, the average overlay can comprise a plurality of overlays with a plurality of sizes and types based a plurality of artificial models, for example, overlays for different age groups, overlays for female and male patients, overlays for patient's having an overbite, under bite, etc. In some variations, the users can manually select an overlay or family of overlays that may fit the teeth of the patient and may then be guided to match the selected overlay with the teeth of the patient. In some variations the method or apparatus may automatically select an overlay or family of overlays for the patient. For example, the system may be trained to recognize (e.g., using machine learning) images corresponding to a particular type of overlay or family of overlays. Selection may be based on patient information provided by the user (e.g., patient age, gender, etc.) or based on prior dental record information specific to the patient.

Figure 3A:
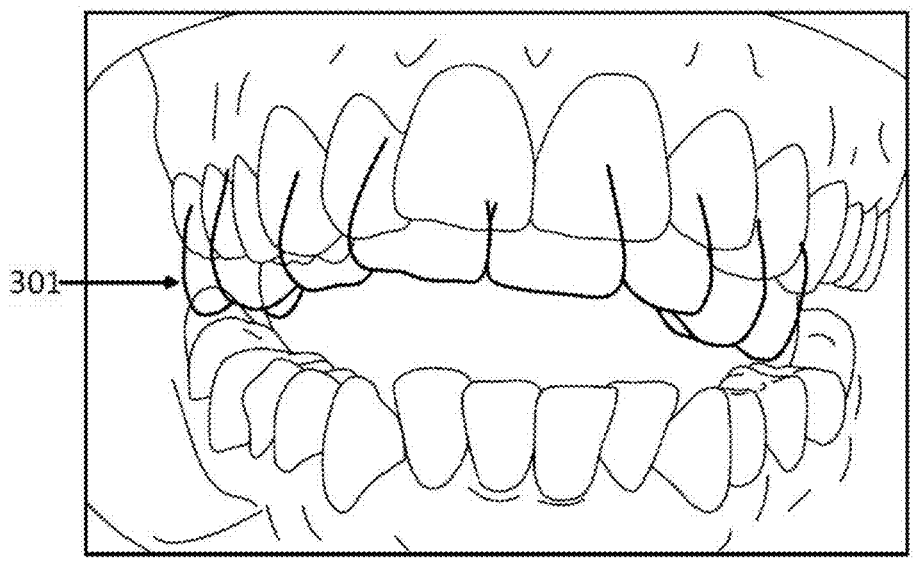
FIG. 3A illustrates an example of a patient-specific overlay according to another embodiment of the disclosure.

In some other embodiments, the overlay can be a patient-specific overlay derived from the patient's teeth. An example of a customized overlay is shown in FIG. 3A. In some variations the apparatus (e.g., software/application software) may image the user's teeth or may receive data derived from a scan, including a digital scan, of the users teeth, and may generate an overlay, such as the outline overlay shown in FIGS. 2A-2C. For example, the patient-specific overlay 301 can be obtained from a specific model of teeth for a specific patient and/or from 3D scan or 3D impressions of the teeth of the patient. This may provide optimal matching for positioning the handheld electronics (e.g., smart phone) when taking the image(s).

Figure 3B:
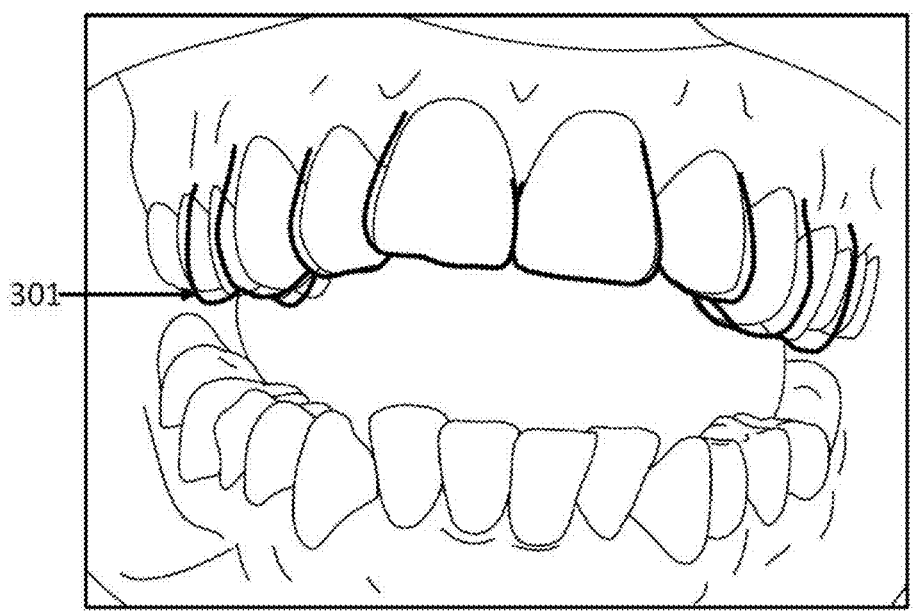
FIG. 3B illustrates an example of an indicator which is triggered when the overlay approximately matches with the patient's teeth. The trigger may be visual (including changing the color of the overlay, displaying or flashing an image/icon/color/symbol on the screen, etc.) and/or audible (emitting a ping, tone, etc.), and/or tactile (e.g., vibrating), etc.

Aligning may be done manually by the user, manually, semi-automatically, or automatically. For example, any of the methods and apparatuses described herein may be used to indicate (e.g., by visual and/or audible and/or tactile) image that the teeth are aligned in the frame with the overlay. For example, FIG. 3A illustrates an example of automatic detection of alignment in real-time with a patient's teeth and an overlay. In FIG. 3A the overlay (which may be displayed in a first color, such as red) shows lines that illustrate the outline of teeth in a first desired predetermined view (e.g., frontal), when the patient's teeth are not aligned with the overlay. Once the apparatus (e.g., software/application software executing on the apparatus) determines that the teeth are in approximately aligned with (e.g., approximately match) the overlay, as shown in FIG. 3B, the screen may display an indicator, such as, in FIG. 3B, by changing the color of the overlay from the first color to a second color (e.g., green, blue, etc.) and/or automatically taking the image. Note that the method or apparatus may automatically determine alignment (a match or approximate match) between the overlay and the patient's teeth in a variety of ways. For example, the method or apparatus may determine alignment when a threshold amount/percentage of the edges of the patient's teeth in the image are within a predetermined minimum distance of the overlay. For example, alignment may be indicated when greater than 50%, greater than 60%, greater than 70%, greater than 80%, greater than 90%, etc. of the edges (e.g., the outer perimeter of the patient's teeth) of the teeth are within about 1 mm, about 0.5 mm, about 0.1 mm, about 0.05 mm, etc.). The edges of the teeth may be determined by any appropriate technique (e.g., edge detection image processing, etc.).

As mentioned, in general, the overlay may be generic, categorical (e.g., appropriate for all patients having one or more citatory-related characteristics) or specific to the patient. The overlay can be a treatment-specific overlay. The teeth of a patient can change. For example, the teeth of the patient can change over time including with treatment. The overlay can be modified according to the predicted or actual changes of teeth of the patient with treatment (e.g., sequential alignment treatment), thus matching the teeth of the patient more precisely. The patient specific overlay or treatment specific overlay can give user's real-time insight into the treatment progress.

During the imaging procedure, users can view the patient's teeth, for example, on the screen of the mobile telecommunications device. Users can further display, on the screen, the overlay comprising the outline of teeth in a predetermined view, wherein the overlay is displayed atop the view of the patient's teeth. The overlay can be an average overlay, or a patient specific overlay, or a treatment specific overlay. Users can move the mobile telecommunications device relative to the patient's teeth so that the overlay approximately matches the patient's teeth in the view of the patient's teeth. Users can then capture an image of the view of the patient's teeth.

As mentioned, the method can further comprise estimating the quality of contour matching between the outline of the overlay and the teeth of the patient in order to help take high quality photos. When the patient's teeth are located on expected place and at the right angle, the overlay approximately matches the patient's teeth in the view of the patient's teeth. The method and apparatuses described herein can help prevent accidently confusing view or angle, and may comprise real-time reaction on the image on the screen of the mobile telecommunications device. Interactive contour matching estimation can enable capturing high quality dental images. The method can comprise real-time interactively estimating contour matching between the outline of the overlay and the teeth of the patient, for example, by using an indicator. In some embodiments, the methods and apparatuses can automatically detect matching between the patient's teeth on the screen and the overlay to confirm the position of the teeth.

Thus, the methods and apparatuses disclosed herein may trigger an indicator when the overlay approximately matches with the patient's teeth. The method or apparatus can automatically capture (or enhance manual capture of) an image of the view of the patient's teeth when the indicator is triggered as shown in FIG. 3B. Users can move the mobile telecommunications device relative to the patient's teeth to match the on-screen overlay with the teeth of patient. If the overlay nearly matches the teeth, the indicator can be triggered, which indicates the moment to capture the image, for example, for progress tracking. Alternatively, in some other embodiments, an image of the teeth can be captured automatically by the mobile telecommunications device when the indicator is triggered. In some variations, either manual or automatic triggering of the camera to take the image may result in taking a plurality of images in rapid succession. The focus, lighting, and/or exposure time may be adjusted between these images, and the best image may be used, or the images may be averaged or combed.

The apparatus (e.g., system) described herein may also provide guidance by indicating when the image is too far or too close from the camera. For example the camera output may be analyzed to determine the approximate distance to/from the patient's mouth and this distance compared to an expected distance to take an optimal image. For example, in any of these variations, image processing may be used to identify the patient's face (e.g., facial recognition), mouth (e.g., using machine-learned feature recognition) or other features, such as the nose, eyes, etc. to determine the distance from the camera and/or what regions to focus on. Any of the methods and apparatuses described herein may include the use (either with an overlay or without an overlay) of tooth recognition. For example, an apparatus may be configured to automatically detect one or more teeth and trigger an alert to take an image (or automatically take the image) when the identified tooth or teeth are in the desired orientation, size and/or location on the screen.

As mentioned, the indicator can be triggered by estimating an indicator of the distance between an edge of the patient's teeth in the view of the patient's teeth and the outline of teeth in the overlay. For another example, the indicator can be triggered by estimating an indicator of the distance between an edge of the patient's teeth at two or more regions and the outline of teeth and comparing that indicator to a threshold value. For yet another example, the indicator can be triggered by estimating an indicator of an average deviation of the outline from a contour of the teeth of the patient. The indicator can be triggered by a variety of ways of estimating a match between the outline of the overlay and the teeth of the patient, not being limited to the examples illustrated herein. In general, in any of the example described herein, images taken may be associated (including marking, labeling, etc.) with an indicator of the predetermined view and/or user identification information and/or date information. For example an image such as shown in 3B may be taken and marked "frontal".

The indicator can be a visual indicator, such as a color change as illustrated in FIG. 3B. When the users move the mobile telecommunications device such that the overlay nearly matches the teeth, the outline of the overlay can change color to green. For example, it may be not perfectly match, but each tooth on the contour may coincide with each real tooth on the screen. When the color of the outline changes from red to green, it is indicating the overlay nearly matches the teeth and it is the moment to capture the image.

In some variations the apparatus and methods may include providing one or more visual or audible clues to the user in aligning the images. For example, one or more arrows may be shown on the screen to indicate that the user should move the mobile telecommunications device in a particular direction (or by a particular amount) to align the patient's teeth with the overlay.

For another example, the indicator can be a sound (e.g., tone or voice) which is triggered when the overlay matches the teeth of the patient. For example, the phone can generate a beeping sound and indicate the overlay matches the teeth and it is the moment to capture the image. The method can comprise automatically capturing an image of the patient's teeth when the indicator is triggered and/or permit the user to manually take one or more image.

Automatically capturing an image of the patient's teeth when the overlay approximately matches with the patient's teeth may be triggered by the apparatus. For example, the shutter of the camera of the mobile telecommunications device can be triggered by an internal indicator.

Generally, the methods and apparatuses described herein are configured to take a series of predetermined specific views of the teeth. Thus, the apparatus may be an application software ("app") that guides a user in taking a sequence of specific images. The specific images may be a set that has particular clinical and/or therapeutic significance, such as frontal/anterior (mouth closed), frontal/anterior (mouth open), left buccal (mouth closed/open), right buccal (mouth closed/open), upper jaw, lower jaw, profile, face, etc.

FIGS. 4A-4H illustrate 8 specific overlay images for the required types of photos according to the orthodontic standard, including an anterior view in FIG. 4A, an another anterior view in FIG. 4B, an upper jaw view in FIG. 4C, a lower jaw view in FIG. 4D, a left buccal view in FIG. 4E, an another left buccal view in FIG. 4F, a right buccal view in FIG. 4G, and an another right buccal view in FIG. 4H.

Figure 5B:
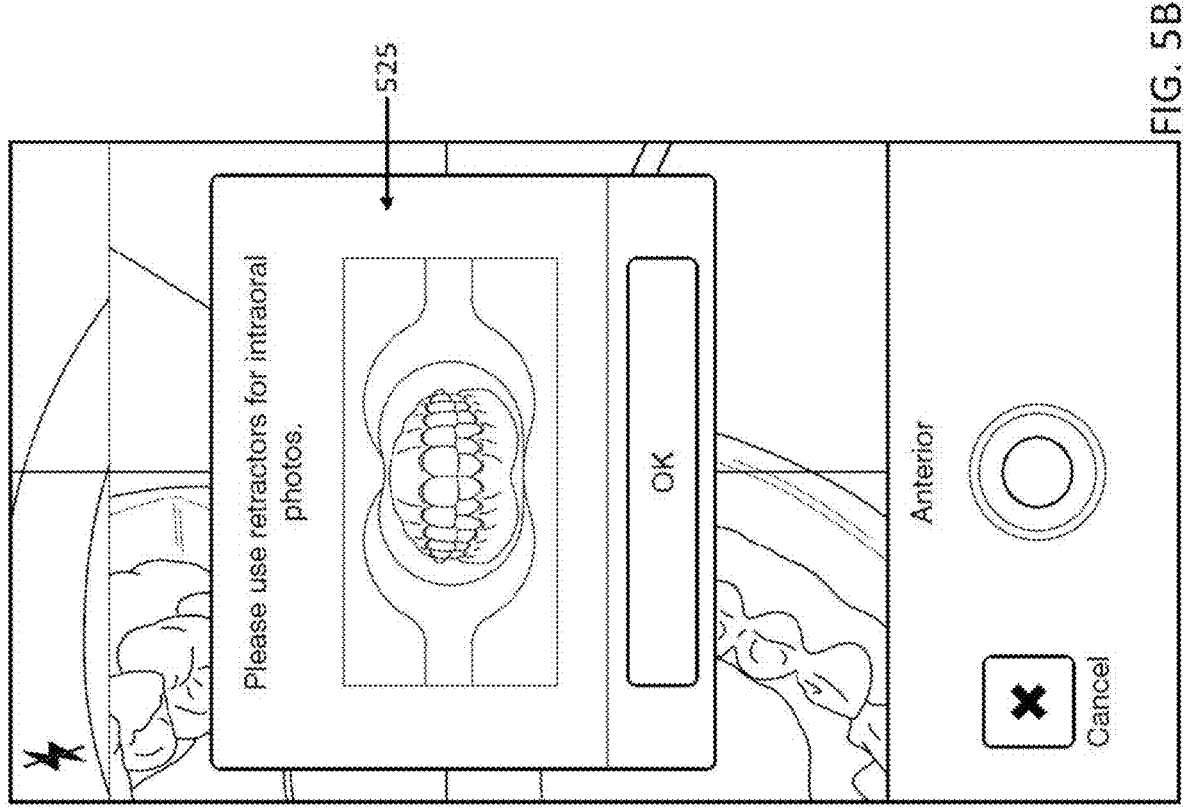
FIG. 5B is an example of on-screen message to guide a user to take dental images.
Figure 5A:
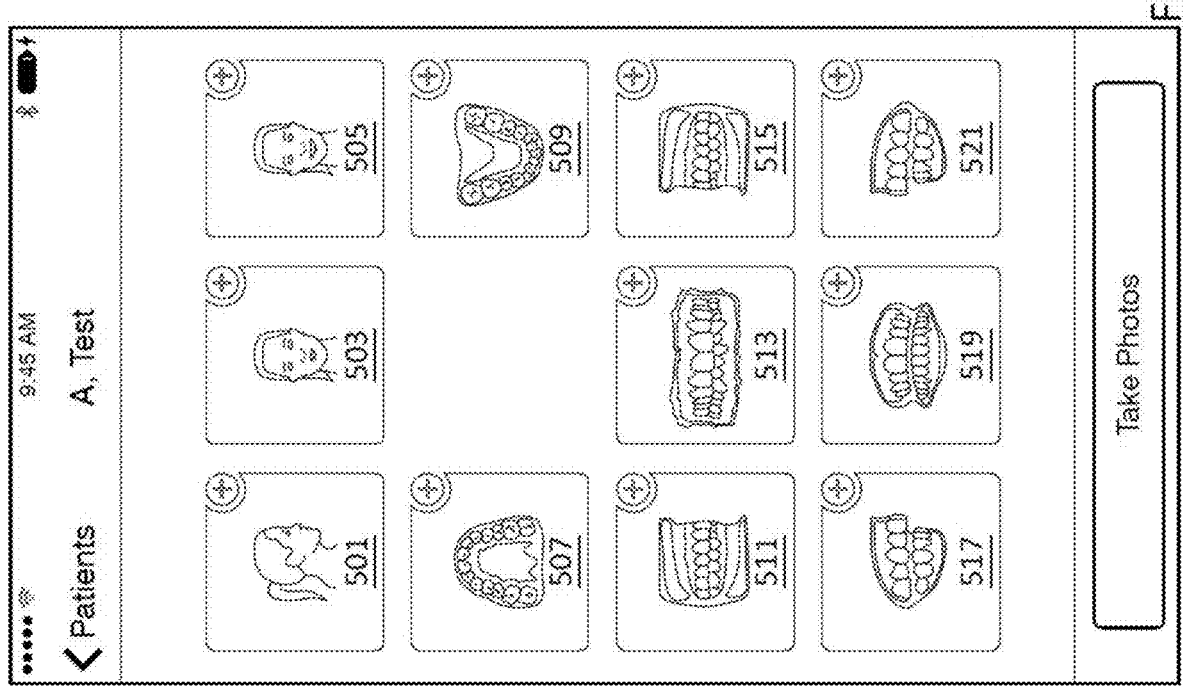
FIG. 5A is an example of a user interface to enable a user to select one of a plurality of overlays for a plurality of dental images in a plurality of predetermined views.

For example, a method to obtain an image of the teeth may include displaying, on the screen, an overlay comprising an outline of teeth in one of an anterior view, a buccal view, an upper jaw view, or a lower jaw view, wherein the overlay is displayed atop the view of the patient's teeth. The method and apparatus may walk the user through taking a complete or partial set of these images. For example, FIG. 5A shows an example of a user interface to enable a user to select one of a plurality of overlays for a plurality of dental images in a plurality of predetermined views, or to show the user what images it will walk them through taking. The predetermined views can include a set of dental images according to known orthodontic standards.

In FIG. 5A, eight views (including three external/head or facial views) are included as part of the predetermined set, including a profile view 501 of the patient's head, a front view 503 of the patient's head, a front view of the patient's head with the patient smiling 505, a view of the upper jaw (from the occlusal surface) 507, a view of the lower jaw (from the occlusal surface) 509, a right buccal view 511 with the jaw closed, an anterior view 513 with the jaw closed, a left buccal view 515 with the jaw closed, a right buccal view with the jaw open, an anterior view with jaw open, and a left buccal view with the jaw open. The apparatus may walk the user through taking each of these views, and may allow the user to select which image to take (e.g., in any order) or may require a predetermined order be used. In addition, as shown in FIG. 5B, the apparatus may provide positioning or other guidance to the user in taking the images. FIG. 5B is an example of on-screen message to guide a user to take dental images with a retractor. The image may be a pop-up message/reminder, which may be optionally disabled, e.g., for experienced users. In FIG. 5B, the message 525 indicates that a cheek retractor should be used (e.g., for the intraoral views such as the upper, lower, anterior, buccal views). In some variations, as described below, the apparatus may automatically detect the cheek retractor, and may use this information to orient the camera, and/or identify the patient's teeth.

Figure 5D:
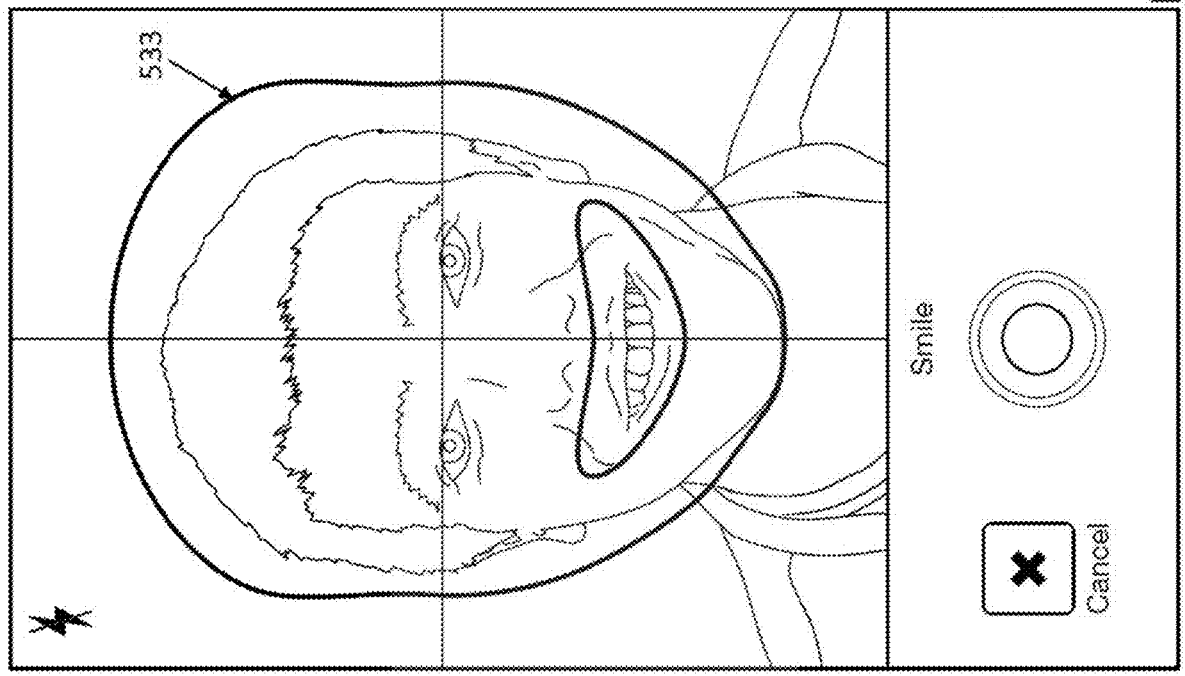
FIG. 5D is an example of a user interface to take a facial image of the patient.
Figure 5C:
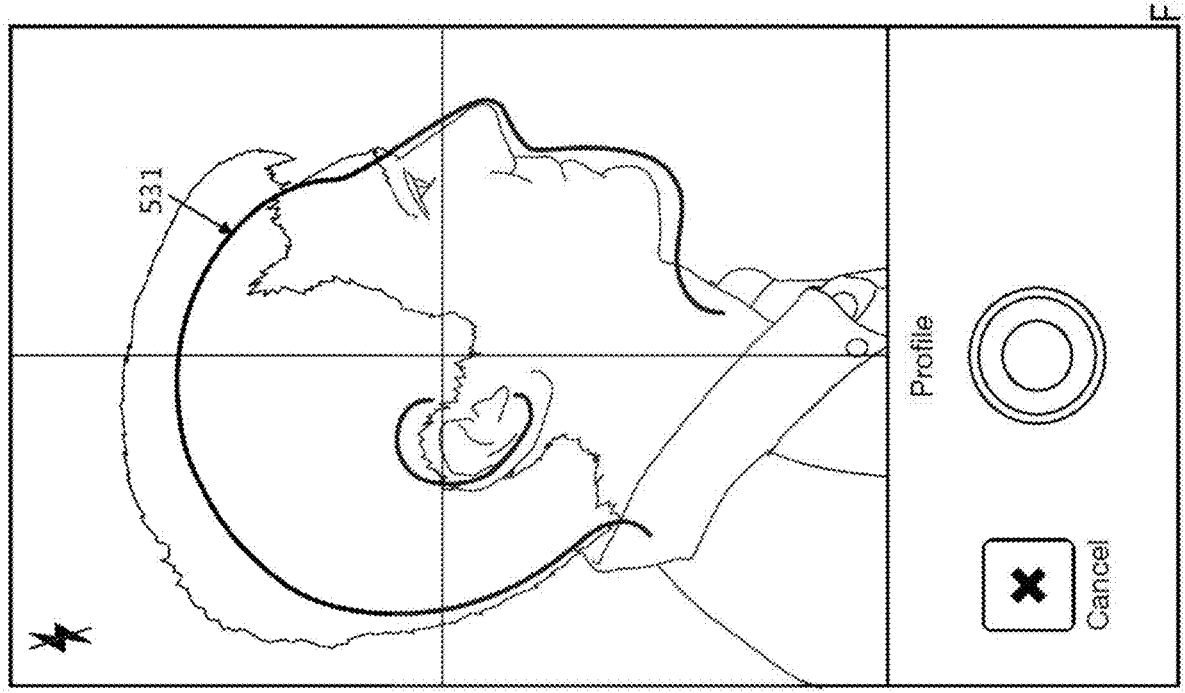
FIG. 5C is an example of a user interface to take a profile image of a patient.

FIG. 5C is an example of a user interface of the apparatus assisting a user in taking a profile image of a patient. In FIG. 5C, the user interface (on the screen of the mobile telecommunications device) shows an overlay of a profile of a patient's head 531. In FIG. 5D the user interface shows an overlay 533 of a facial image of a generic patient. The overlay may include one features, such as ears nose, mouth, etc. In any of these methods and apparatuses facial recognition tools (software tools) may be used to help identify and/or confirm the position of a patient's head and/or teeth.

The method can include display on a user interface a plurality of overlays for each of a plurality of dental images in a plurality of predetermined views. As mentioned above, the user can select one of the overlays. For example, there can be three different facial images and 8 different dental images as shown in FIG. 5A. For each required views of the dental images, there can be an open position image and a closed position image.

The method can further allow the users to take more images of their choice. For example, the method can have a user interface to allow a user to input an angle and a distance of his or her choice, thus giving the user freedom to capture custom images. In some embodiments, the method can further enable the user to take several photos in motion to restore 3D structure of the teeth.

Figure 6B:
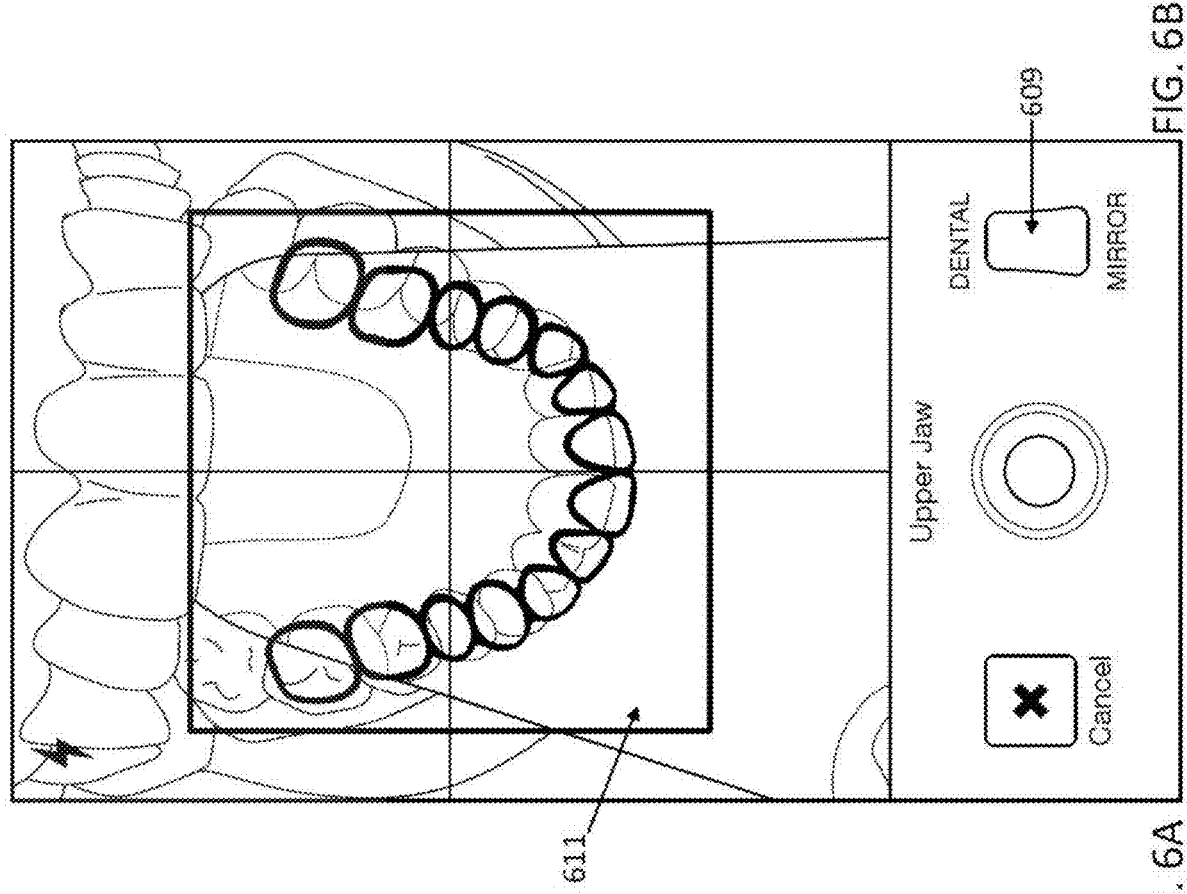
FIG. 6B is an example of a poor quality image of the teeth.
Figure 6A:
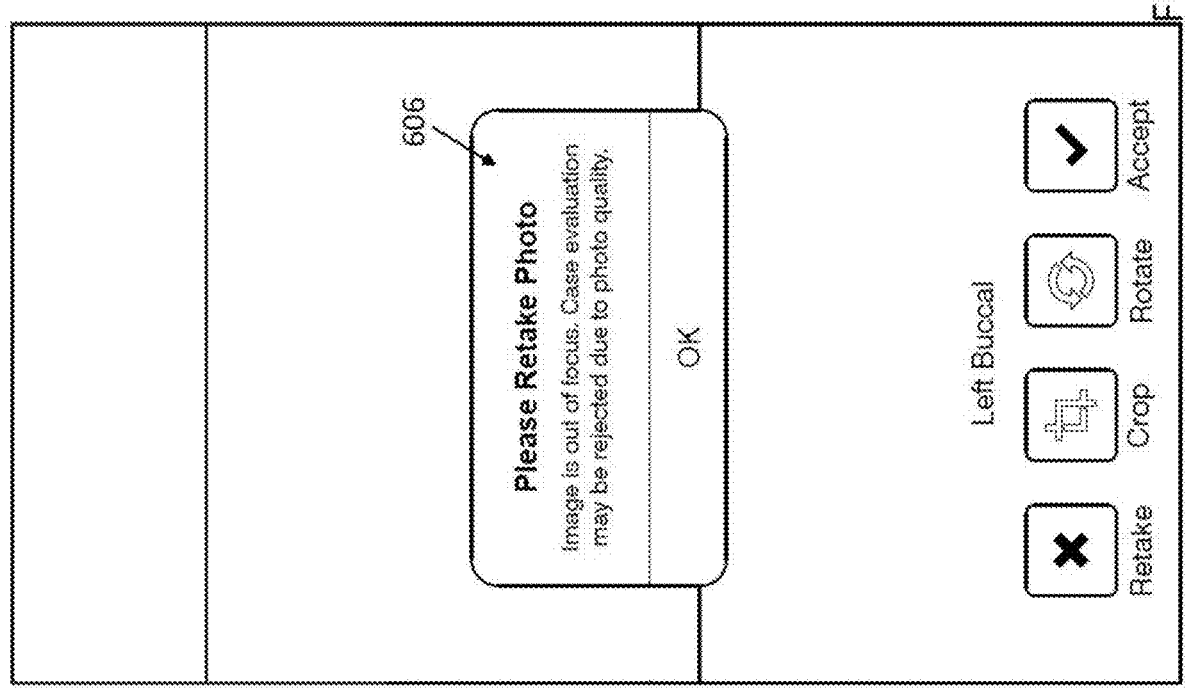
FIG. 6A is an example screenshot which indicates the captured image is out of focus after reviewing the image quality.

Any of these methods and apparatuses may further include reviewing the captured image on the mobile telecommunications device to confirm image quality and/or automatically accept/reject the image(s). For example, a method or apparatus may be configured to check the image quality of the captured image and displaying on the screen if the image quality is below a threshold for image quality. FIG. 6A is an example of a user interface having a notification window 606 that indicates the captured image is out of focus after reviewing the image quality. FIG. 6B is an example of a poor quality image of the teeth. In some other embodiments, the method can comprise automatically filtering out images of bad quality such as blurred, wrong angle of view, etc. For example, when the image is too dark or some of all of the teeth are blocked, as shown in FIG. 6B, the image can be excluded and the user required to take an alternative image.

In FIG. 6B, the apparatus also indicates that a dental mirror 609 should be used to take the upper jaw image. The apparatus may be configured to automatically detect when the dental mirror is present, for example, by detecting a reflection or a symmetry within the image field. In FIG. 6B, the mirror 611 includes an excess of reflected light.

The method can comprise evaluating the image quality and warning doctors if the image might be rejected. For example, if the image is too dark, or blurry, or out of focus, a warn message is shown on the screen to warn the doctors to retake the photo. The quality of the image can be evaluated and reviewed by a variety of methods. For example, the method can comprise evaluating the focus status of the image. For another example, the method can comprise analyzing the image using a library. For yet another example, the method can comprise analyzing the brightness of the image. In some embodiments, the method can further comprise using image recognition algorithms to ensure that all required teeth are visible.

Figure 7B:
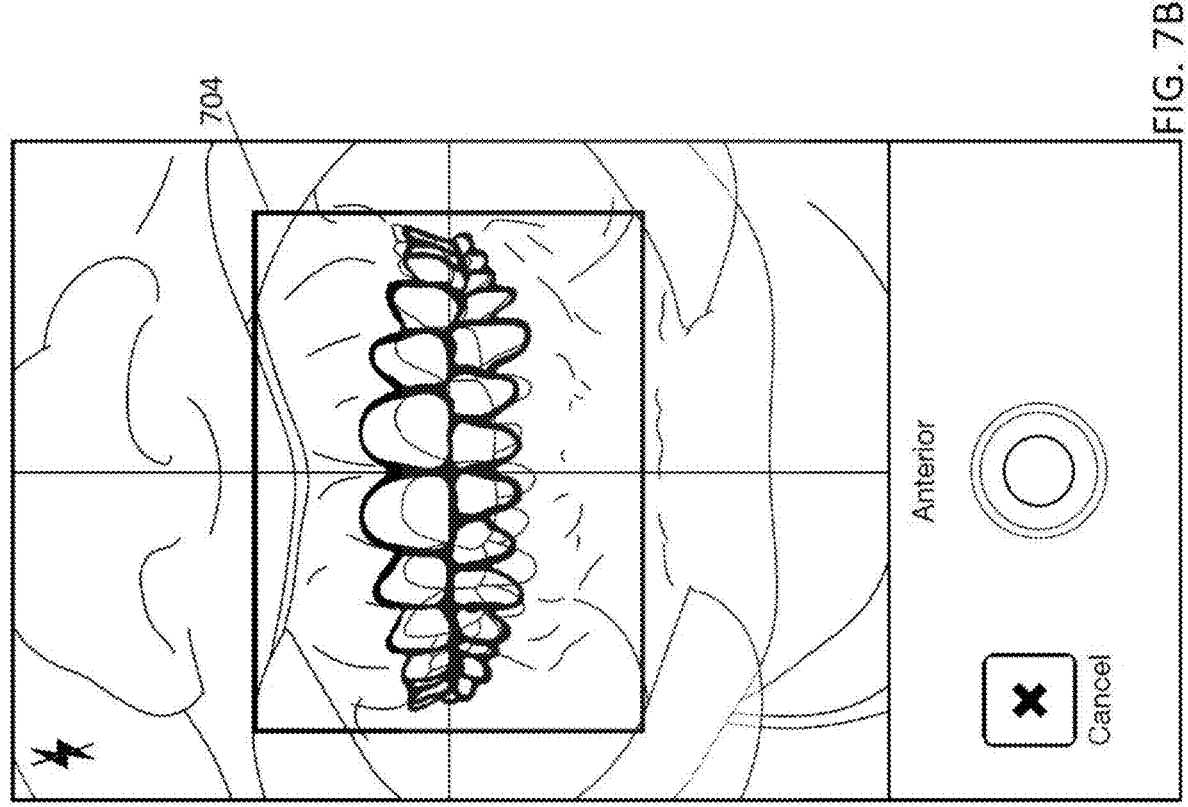
FIG. 7B shows another example overlay comprising a cropping frame and an outline of teeth in anterior view.
Figure 7A:
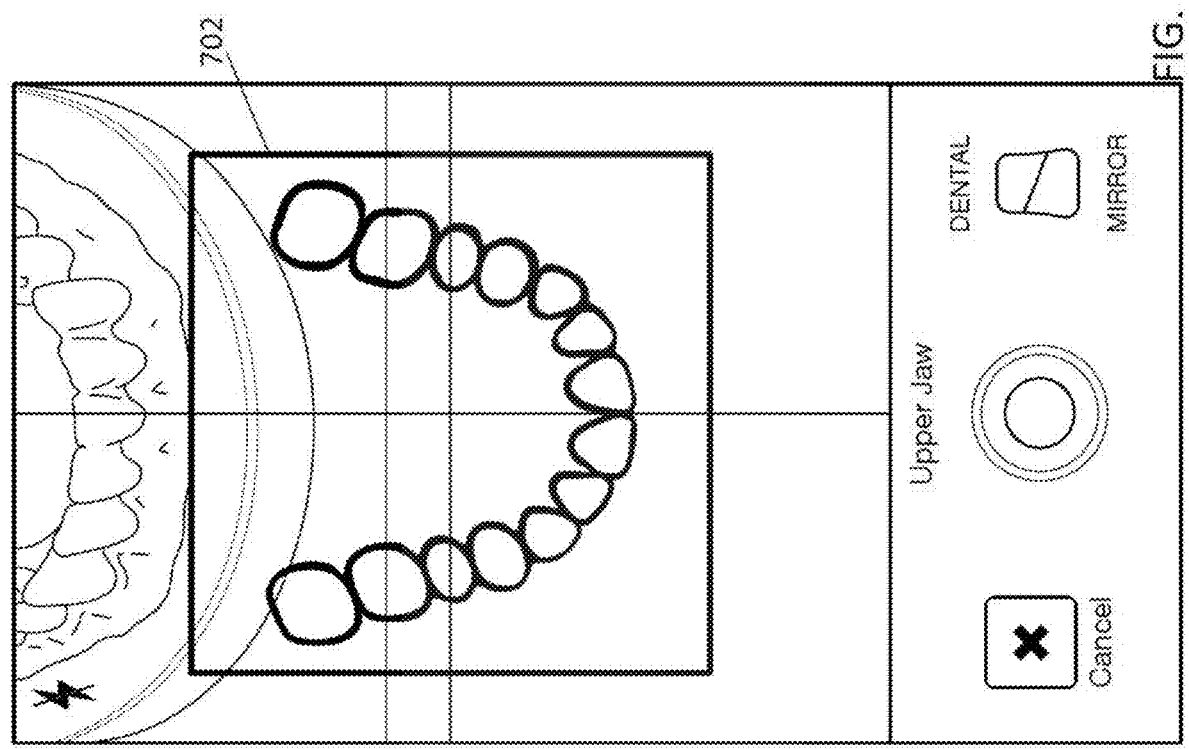
FIG. 7A shows an example overlay comprising a cropping frame and an outline of teeth in an upper jaw view.
Figure 7C:
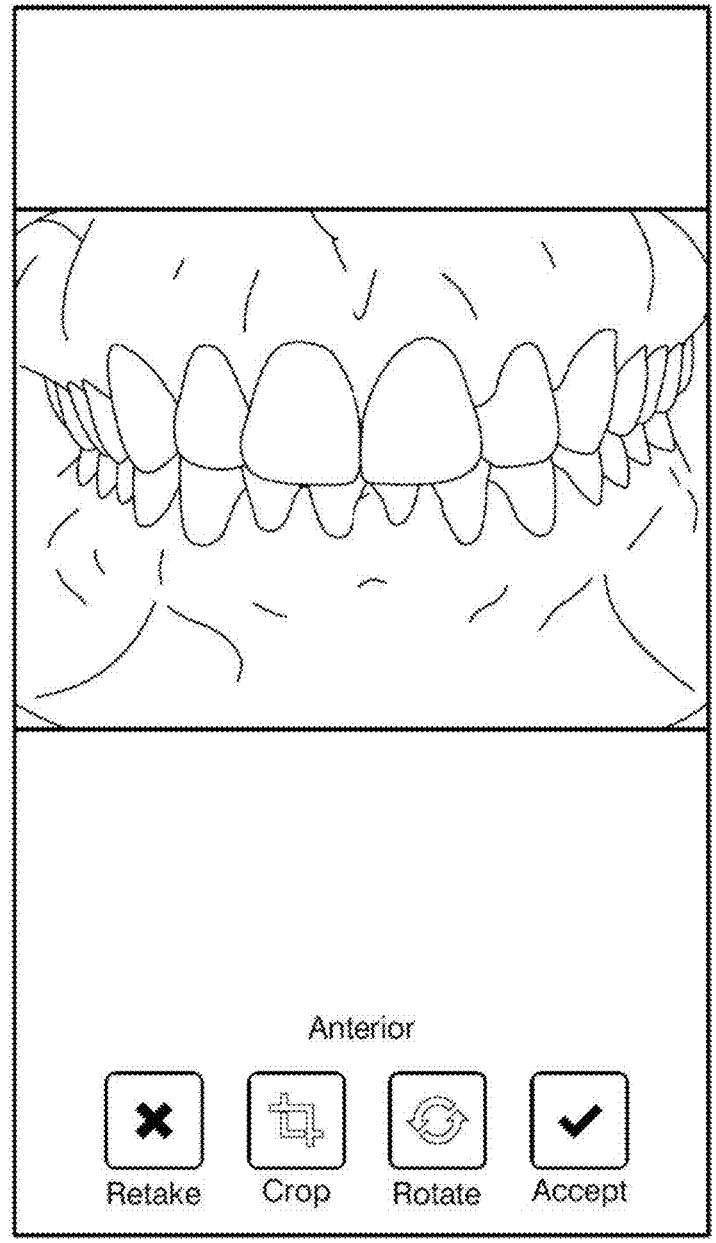
FIG. 7C shows an example of an image captured using the overlay of FIG. 7B.

FIG. 7A shows an example overlay comprising a cropping frame and an outline of teeth in an upper jaw view. FIG. 7B shows another example overlay comprising a cropping frame and an outline of teeth in anterior view. In some embodiments, the method can further comprise displaying, on the screen, an overlay comprising a cropping frame and an outline of teeth in one of an anterior view, a buccal view an upper jaw view, or a lower jaw view, wherein the overlay is displayed atop the view of the patient's teeth. The method can further comprise automatically cropping the captured image as indicated by the cropping frame.

Often doctors have to wait one or more days to crop and edit the dental images before uploading the images, the method described herein can further comprise displaying the overlay with the cropping frame and the outline of teeth in the predetermined view, and automatically cropping the captured image. FIG. 7A illustrate a cropping frame 702 in the upper jaw view of teeth. FIG. 7B illustrate another cropping frame 704 in the anterior view of teeth. By matching the overlay, the method can automatically crop the image to get the correct view of the teeth. Once the photo is taken, the doctors can still re-crop and edit later.

Figure 8A:
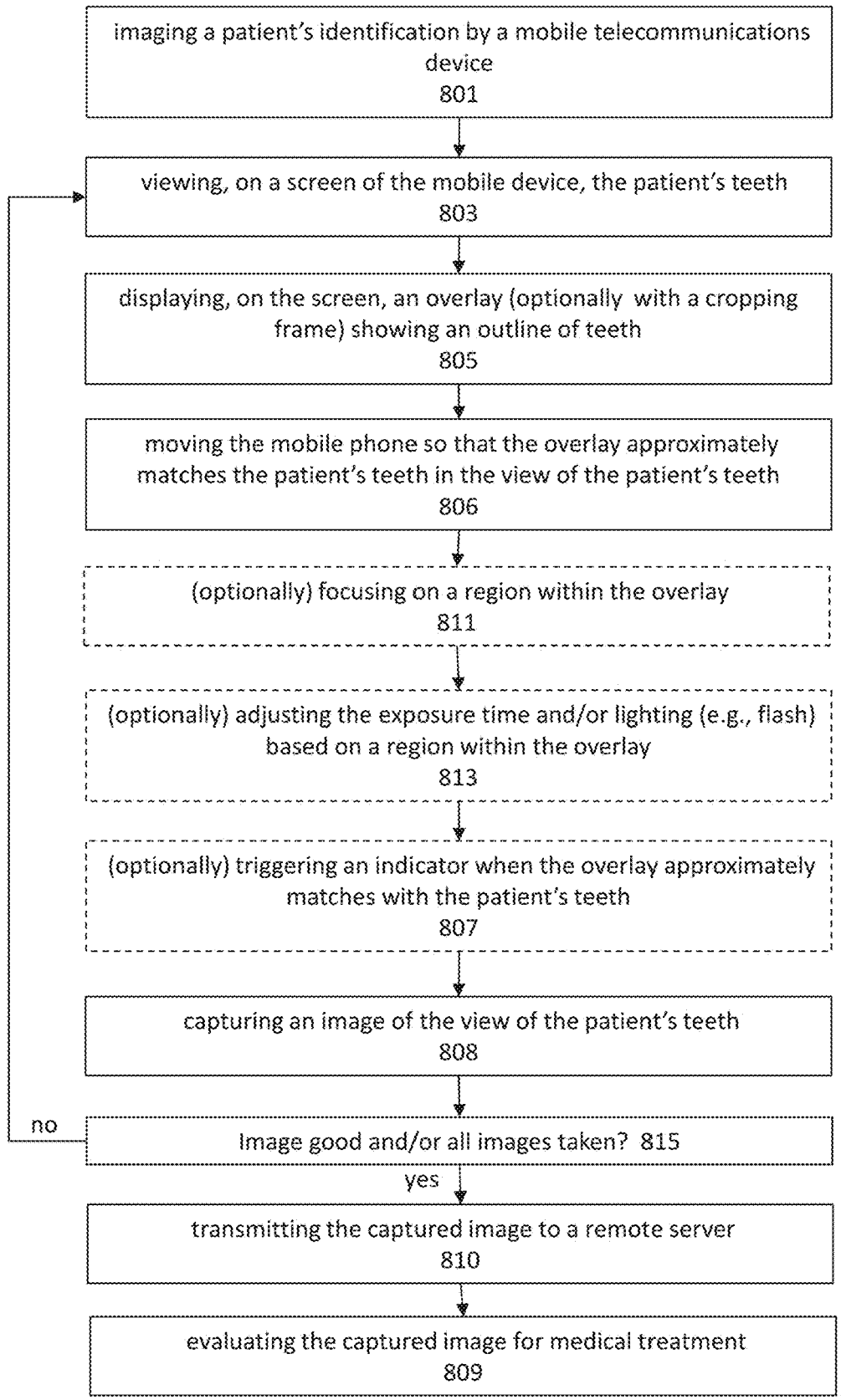
FIG. 8A is an example of a block diagram of a method to obtain an image of teeth of a patient.

FIG. 8A is an example of a block diagram of a method to obtain an image of teeth of a patient. A user (e.g., dental professional, such as a doctor, orthodontist, etc.) may get quick feedback of treatment progress and/or assessment of treatment suitability. As shown in FIG. 8A, the method can include (optionally) using patient ID for authorization in step 801. For example, the method can comprise imaging a patient's identification using a mobile telecommunications device. The method can further comprise automatically populating a form with user identification information based on the imaged identification.

In general, a method for obtaining a series of images of a patient's teeth can include viewing, on a screen of the mobile telecommunications device (in real time), the patient's teeth as shown in step 803. The method can also include displaying, on the screen, an overlay comprising a predetermined view and (optionally a cropping frame). The overlay of the predetermined view may be, for example: an anterior view (jaws open or closed), a buccal view (left, right, and jaws open/closed) an upper jaw view, or a lower jaw view, etc. The overlay may be displayed atop the view of the patient's teeth as shown in step 805. As described herein the method or apparatus performing the method may be configured to include a selection step for determining which overlay to use (e.g., by automatic identification of teeth/face shown in the screen and/or by user manually selecting from a menu, etc.). For example, the method can further comprise enabling the user to choose the predetermined view. A user interface may show the user a predetermined view and a plurality overlays for a plurality of predetermined photo views (for example, anterior (open/closed), left buccal (open/closed), right buccal (open/closed), occlusal maxillary (upper jaw), occlusal mandibular (lower jaw), etc.). The user can select one of the plurality overlays to capture the corresponding dental images. For each predetermined view, the overlay with an outline is shown on the screen of the mobile telecommunications device. The method can further comprise moving the mobile telecommunications device so that the overlay approximately matches the patient's teeth in the view of the patient's teeth as shown in step 806. For example, the method can further comprise displaying instructions about positioning the patient's teeth on the screen of the mobile telecommunications device prior to displaying the overlay. Optionally, as described herein, the method may include using the overlay region to adjust the focus 811, lighting, exposure 813, etc.

In some embodiments, the method can further comprise triggering an indicator when the overlay approximately matches with the patient's teeth as in (optional) step 807. For example, if the overlay is not matched, it will be displayed using red color. If the overlay matches the teeth, the color of the outline changes to green. The method can further comprise capturing an image of the view of the patient's teeth as shown in step 808. Steps 803 to step 808 can be performed for each predetermined photo view 815. The user may take several photos for each view for more accurate treatment progress estimation. The method can further comprise repeating the steps of viewing, displaying, moving and capturing to capture anterior, buccal, upper jaw and lower jaw images of the patient's teeth. In addition, the apparatus may check the image to be sure that the quality is sufficiently high (e.g., in focus, etc.); if not, it may repeat the step for that view.

The method can further comprise transmitting the captured image to a remote server as in step 810 and/or evaluating the captured image for medical treatment by using the set of images collected 809. The captured dental images can be transferred to server part for performing more precise estimation of treatment progress and/or for pre-screening a patient. For example, the captured dental images can be used for case evaluation before starting aligner treatment to evaluate if the patient is a candidate for the treatment as described in FIG. 8B. The captured dental images can also be used to set up case property when doctors start the treatment, for example, the captured images can be used to fills prescription forms. The captured dental images can further enable doctors to track treatment process and give them real time clue or feedback of treatment process.

In FIG. 8B, a method of remotely pre-screening a patient for an orthodontic treatment may incorporate any of the steps of FIG. 8A. In FIG. 8B, the method first includes guiding a user, with a mobile telecommunications device having a camera, to take a series of images of the patient's teeth in a plurality of predetermined views by sequentially 851, for each predetermined view. As mentioned, an of the steps described above for FIG. 8A may be used, including but not limited to: displaying, on the screen, an overlay comprising an outline of teeth in one of the predetermined views from the plurality of predetermined views, wherein the overlay is displayed atop an image of the patient's teeth 855. Any of these methods may also include capturing the image of the patient's teeth when the overlay approximately matches the patient's teeth in the view of the patient's teeth 857. Once the full set of images (and any additional information, including camera position for each image, label of image, date of series, etc.) are collected, they may then aggregated into a single set. This information may then be transmitted (e.g., including the series of images) to a remote location to determine if the patient is a candidate for the orthodontic treatment based on the series of images 859. Thereafter, the method may display, on the screen of the mobile telecommunications device, an indicator that the patient is, or is not, a candidate for the orthodontic treatment 861.

Figure 9:
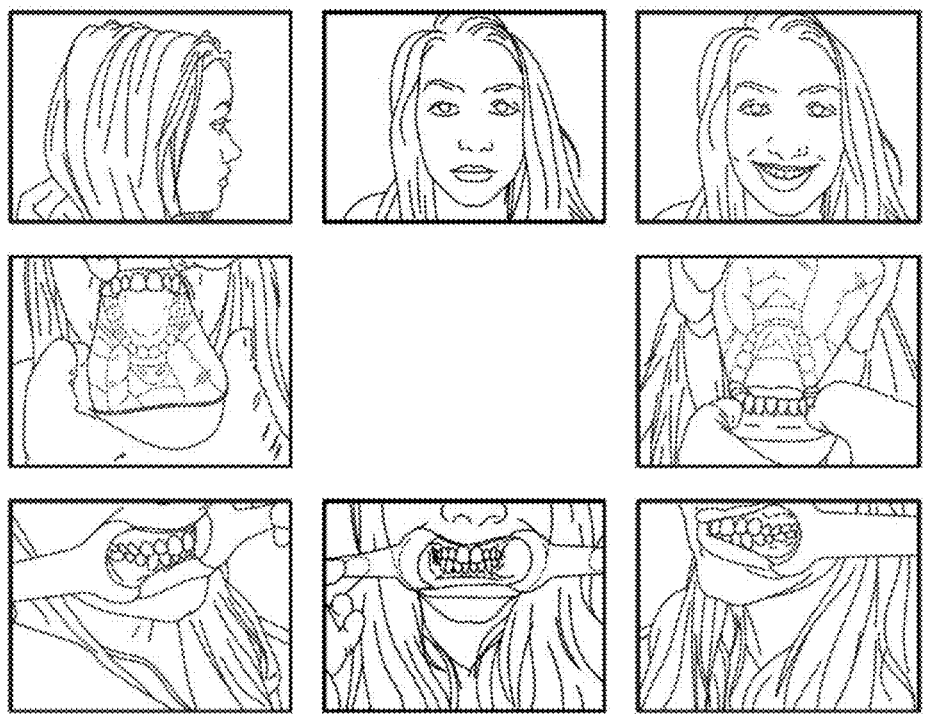
FIG. 9 is an example of a set of facial and dental images of a patient captured by using a digital SLR camera.
Figure 10:
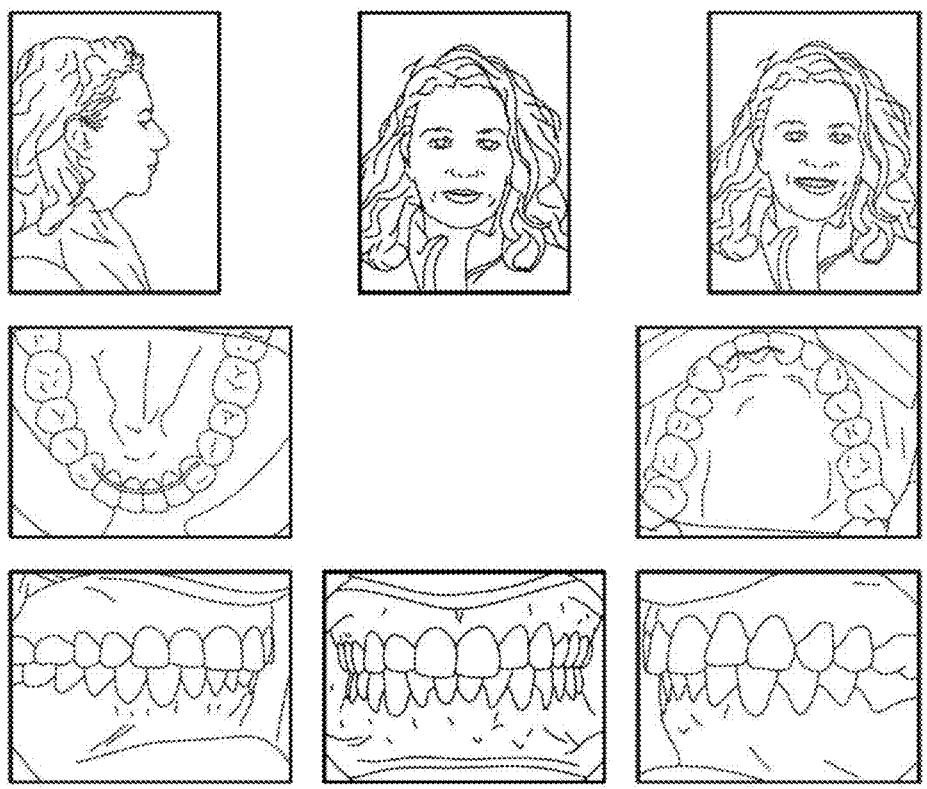
FIG. 10 is an example of a set of facial and dental images of a patient captured by using a mobile telecommunications device through the method disclosed herein.
Figure 11A:
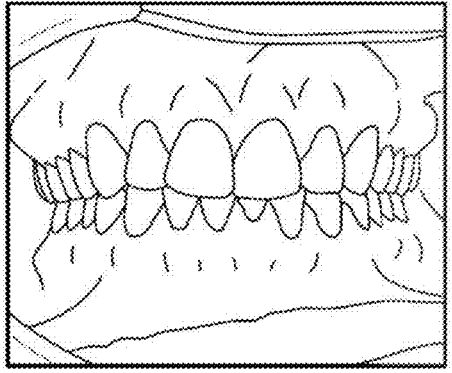
FIGS. 11A-11H are examples of a set of dental images captured by using the mobile telecommunications device through the method disclosed herein.
Figure 11C:
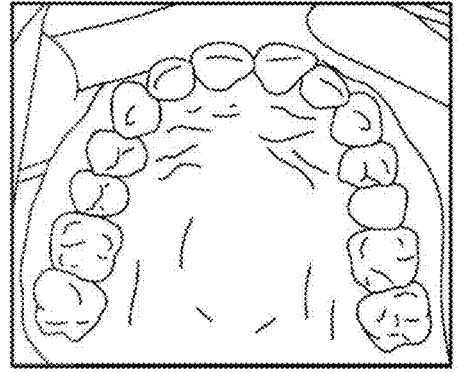
Figure 11B:
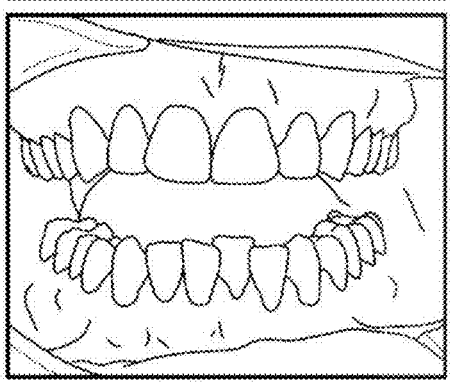
Figure 11D:
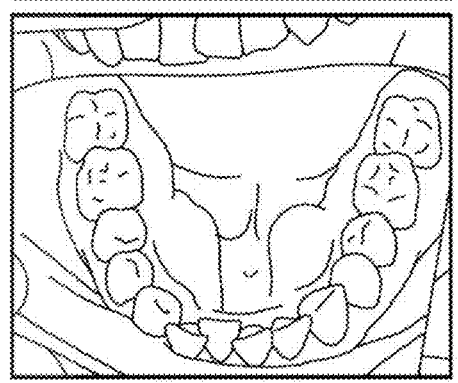
Figure 11E:
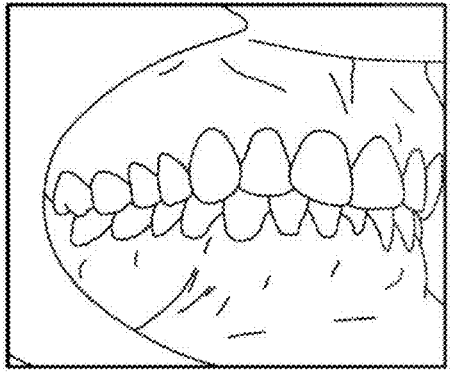
Figure 11G:
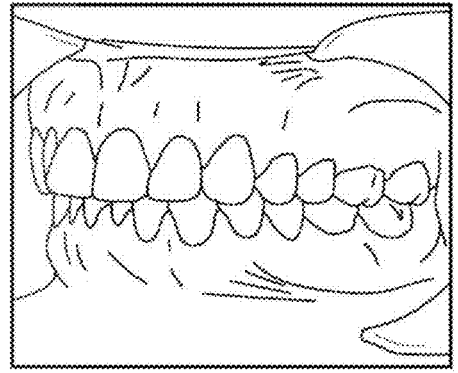
Figure 11F:
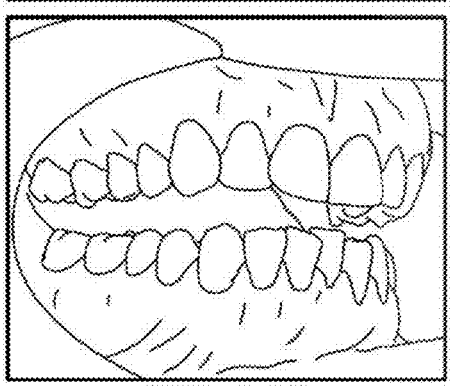
Figure 11H:
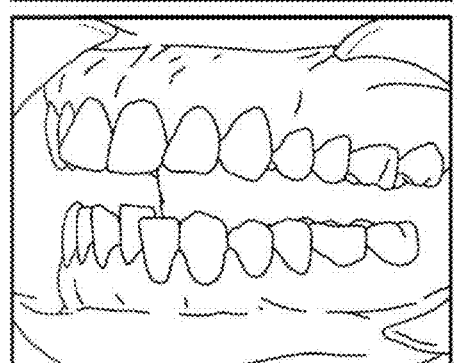

FIG. 9 is an example of a set of facial and dental images of a patient captured by using a digital SLR camera. In FIG. 9, the images include 8 images: profile, frontal, frontal with smile, upper jaw, lower jaw, right buccal (closed jaws), anterior (closed jaws), and left buccal (closed jaws). FIG. 10 is an example of a set of facial and dental images from these same views, captured by using a mobile telecommunications device through the method disclosed herein. FIGS. 11A-11H are examples of a set of dental images captured by using the mobile telecommunications device through the method disclosed herein, showing anterior (FIG. 11A), anterior open (FIG. 11B), upper (FIG. 11C), lower (FIG. 11D), right buccal closed (FIG. 11E), right buccal open (FIG. 11F), left buccal closed (FIG. 11G) and left buccal open (FIG. 11H). As shown in FIGS. 9-11H, the method disclosed herein can enable the users to capture high quality dental images in a plurality of predetermined views to meet the orthodontic standards.

Targeted Focus

Any of the method and apparatuses described herein may include tooth-specific focusing. In general, the camera of the mobile telecommunications device may be configured so that the camera automatically focuses on a tooth or teeth. In variations in which the system is configured to detect a patients teeth within an image, the apparatus may then focus on the teeth automatically. Alternatively or additionally, the apparatus or method may be configured to use the overlay, or a region within the overlay, to focus on the patient's teeth. For example, the apparatus (e.g., a non-transitory, computer-readable storage medium storing a set of instructions capable of being executed by a processor of a mobile telecommunications device having a camera) may be configured to focus on a subset of the region within the overlay on the display, and automatically focus within this region or sub-region. Within this region or sub-region, the camera may be controlled to perform any appropriate type of autofocusing, including but not limited to: contrast-detection auto-focus, phase-detection auto-focus, and laser auto-focus.

For example, the apparatus or method may first disable the camera's native autofocusing, which may default on a particular region (e.g., the central region), motion detection, and/or object (e.g., face) recognition, or some variation of these. The native autofocusing, if used with the overlay and method of matching the overlay to a patient's teeth may instead focus on the lips, cheek retractors, tongue, etc., rather than the teeth or a portion of the teeth. By instead restricting the autofocusing to a region that is limited to the overlay or a portion of the overly, the apparatus and method may instead properly focus on the teeth.

Figure 12A:
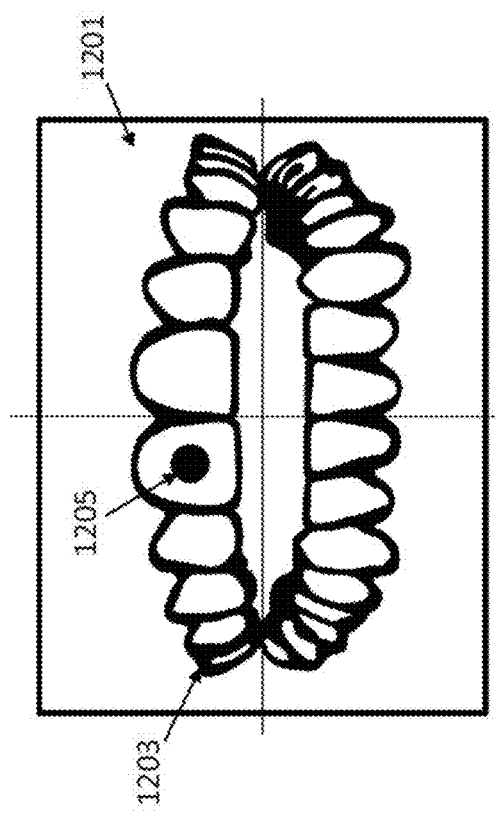
FIG. 12A illustrates a method of focusing within a region of an overlay (shown by the dot on the upper incisor) rather than defaulting to the autofocus of the camera for the mobile telecommunications device.
Figure 12C:
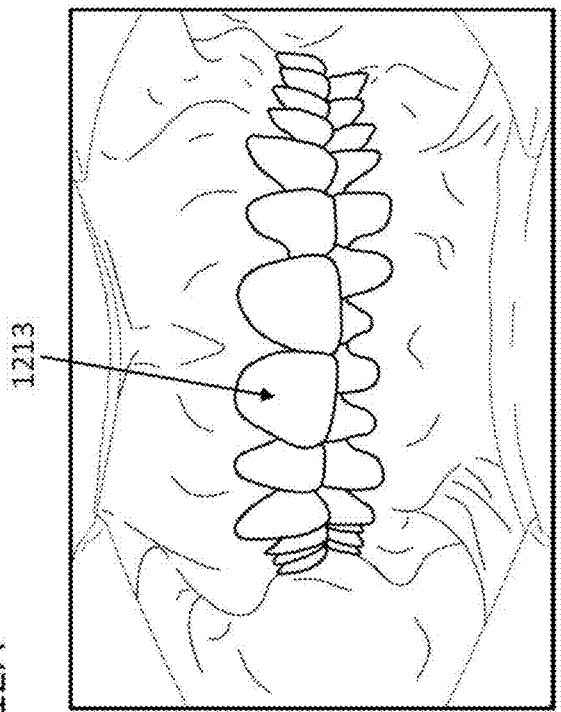
FIGS. 12B and 12C illustrate a comparison between using the default autofocus (FIG. 12B) of a mobile telecommunications device, and the targeted focus (e.g., as shown in FIG. 12A) with the systems and methods described herein, providing a shaper overall focus on the teeth. In the line drawings shown (adapted from photographs) the focus is illustrated by the relative darkness of the lines. The focus may be represented by the darkness of the lines.
Figure 12B:
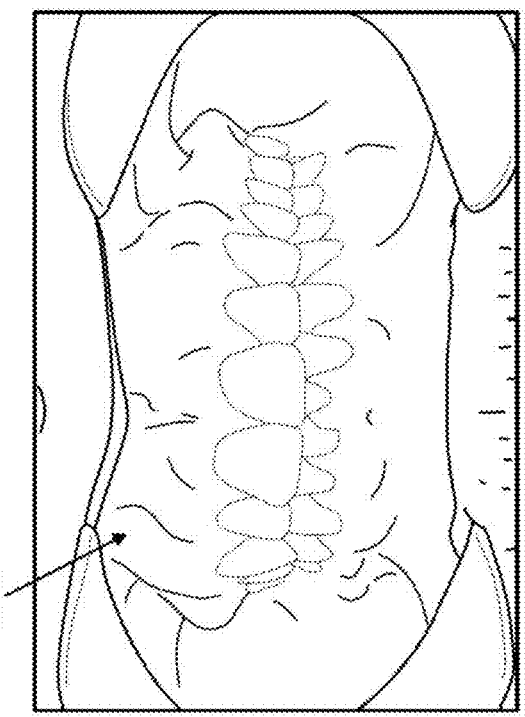

For example, FIG. 12A shows an example of a screen 1201 having an overlay 1203 shown atop any images from the camera being displayed on the screen. In FIG. 12A, a region (point) of focus within the overlay is shown as a dot 1205 within the overlay of one of the upper incisors. Thus, in this example, the point of focus on the screen is shown as the front (incisor) teeth when the teeth are approximately aligned with the overlay. FIG. 12 shows an example of an overlay for an anterior (open mouth) view. Other views may have a point of focus within the overlay centered on different teeth, or more than one tooth. For example, an anterior view may a have a point of focus within the overlay over a bicuspid tooth, or a visible molar, and/or a canine. The user (e.g., doctor, orthodontist, technician, assistant, etc.) may align the patient's teeth with the overlay, and take an image and the mobile telecommunications device may be controlled so that a region within the overlay is automatically controlled to focus within this region of the overlay. In FIG. 12A, and exemplary image shown in FIG. 12C, the focus was limited to on one of the central incisor teeth within the overlay. FIGS. 12B and 12C provide a comparison between an image taken with the patient's teeth generally aligned within an overlay for an anterior (bite closed) image 1211 with the camera for the mobile telecommunications device set to its default autofocusing technique (shown in FIG. 12B, on the left) compared to the targeted autofocusing described above, in which the autofocusing was limited by the apparatus to a region 1213 corresponding to an incisor within the overlay (shown in FIG. 12C, on the right).

Adapted Lighting Mode

Any of the apparatuses and methods described herein may also be configured to automatically and accurately adjust the lighting and/or exposure time so that the teeth are optimally illuminated for imaging, so that details may be apparent. As described above for the autofocusing within the image, the illumination (lighting) may be similarly adjusted by using the overlay or a sub-region of the overlay to set the intensity of the applied lighting, such as the flash.

In general, a camera of a mobile communications device may include a light source providing illumination when taking an image. The camera may have one or more lighting modes for operation, including, for example, a bust flash (a pulse or flash of light correlating with image capture), torch (a continuously on light), or no flash/no illumination (e.g., not providing illuminated). Any of the methods and apparatuses described herein may improve the images of the patient's teeth that are captured by automatically selecting and controlling a particular lighting mode for each image captured (e.g., each predetermined view). For example, in particular, the apparatus may be configured by adjusting or controlling the lighting mode so that no flash is used when taking the facial images (e.g., profile facial images, frontal facial images, with or without smile, etc.); the lighting mode may be set to burst flash when taking the occlusal images (e.g., upper occlusal/upper jaw and lower occlusal/lower jaw); and torch illumination may be automatically selected when taking intra oral photos (e.g., anterior views, buccal views etc.). The intensity of the flash may also be adjusted. For example, the intensity of the light applied may be adjusted based on a light level detected from the region of an image within an overlay on the screen. In some variations the choice to use any additional illumination at all may be made first, based on the light intensity within the overlay region; if the light level is below a threshold (e.g., within the lower 5%, 10%, 15%, 20%, 25%, 30%, etc. of the dynamic range for intensity of light for the camera of the mobile telecommunications device) within all or a portion of the overly, then then lighting mode may be selected based on the type of predetermined view for the overlay. For example, if the overlay shows an intra oral view (e.g., anterior, anterior mouth open, buccal, buccal mouth open, etc.) then the lighting mode may be set to torch, and in some cases the level of brightness of the torch may be adjusted based on the light level detected within the overlay. If the overlay corresponds to an occlusal view (e.g., upper jaw, lower jaw) then then lighting mode may be set to burst flash, and in some cases the level of brightness of the torch may be adjusted based on the light level detected within the overlay.

Figure 13B:
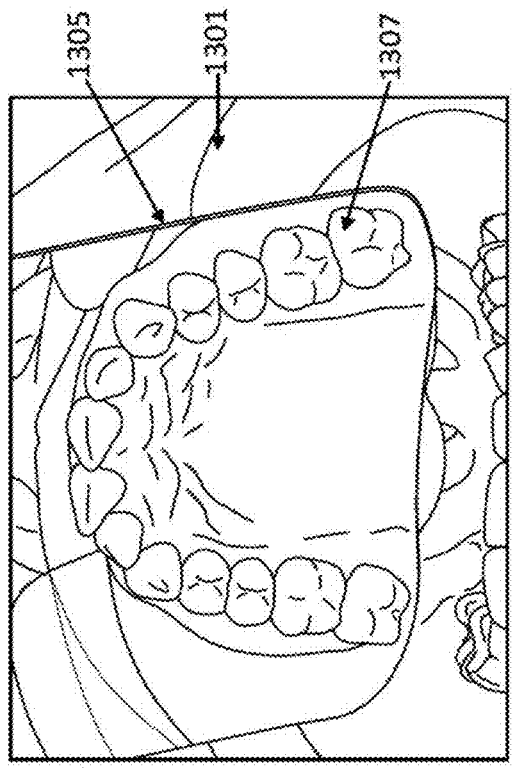
FIGS. 13A and 13B show a first example of a comparison between using the default focus and lighting (flash), as shown in FIG. 13A, compared with using a region within the overlay (overlay not shown in FIGS. 13A and 13B) to set the focus and lighting level.
Figure 13D:
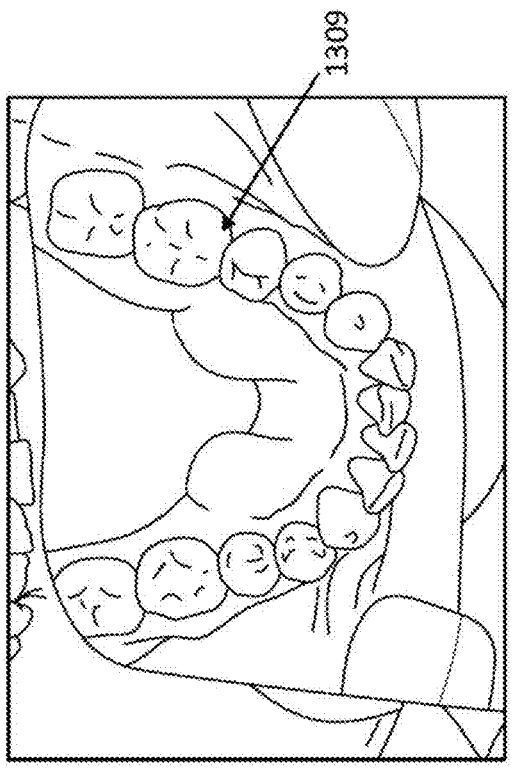
FIGS. 13C and 13D illustrate another example of a method of using a region within the overlay (overlay not shown in FIGS. 13A and 13B) to set the focus and lighting level.
Figure 13A:
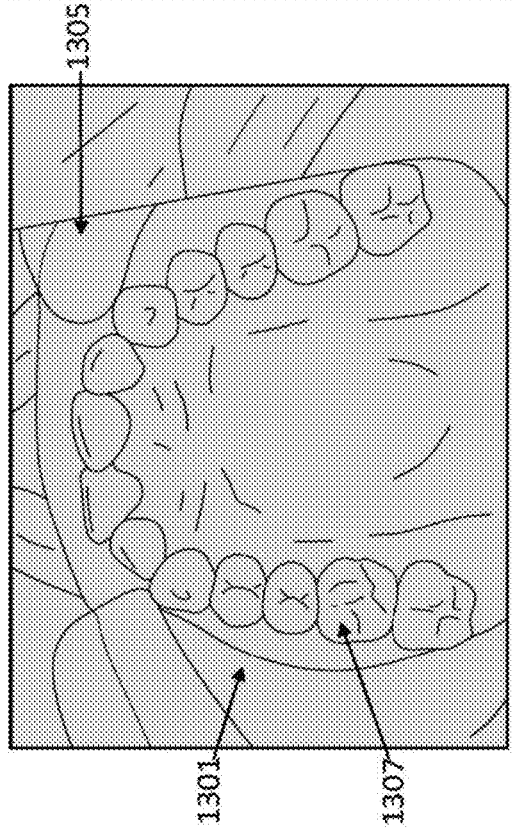
Figure 13C:
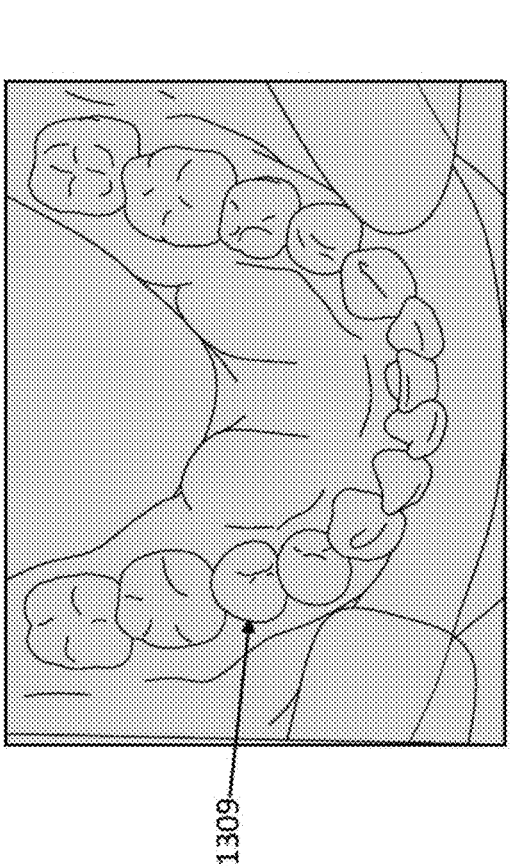

FIGS. 13A-13B and 13C-13D illustrate comparisons between images of the teeth taken guided by an overlay (not visible on the images shown). FIG. 13A shows an upper jaw, occlusal view, taken with a dental mirror using the default focusing and with no flash. For comparison, FIG. 13B shows the same teeth with the focus limited to a sub-region of the overlay (not shown) and the flash on as a bursting flash. In FIG. 13B, additional details of the teeth 1307 in the upper jaw, as seen with the dental mirror 1305, as visible. FIGS. 13C and 13D show a similar example, in which the lower jaw 1309 is imaged without limiting the focus to the overlay region (FIG. 13C) and without a flash (e.g., flash in the 'off' mode). For comparison the same predetermined view of the teeth is shown in FIG. 13D with the focus adjusted to a region within the overlay for the lower teeth and with the flash automatically adjusted to be on (torch mode). A dental mirror was used to capture this image as well.

Thus, any of the methods and apparatuses described herein may automatically adjust the illumination provided by switching on or off the automatic flash and/or by setting the light level, or allowing the user to adjust the light level(s). For example, the method of apparatus may toggle between automatic flash, no flash/illumination, user-adjusted light level ("torch mode") or automatically adjusted light level, based on one or more of user preferences and the image to be taken. For example, when taking a profile or face image, the apparatus may be configured so that the flash is turned on, e.g., defaulting to the camera's auto-flash function, if one is present. When taking an intraoral images (e.g., an anterior view, a buccal view an upper jaw view, or a lower jaw view, etc.) the flash may be turned off, and instead the apparatus may be adjusted to use a "torch" mode, in which the light is continuously on, particularly when imaging. The level of the light may be set automatically, as mentioned above, or it may be adjusted by the user. For example, when taking intraoral images of the teeth, the torch function of the camera light may be set to be on at a level that is approximately 10-50% of the peak intensity (e.g., between 15-40%, between 20-30%, etc.). In some variations the torch intensity may be adjusted in real time based on the image quality, and in particular, based on the light level of a region within the overlay (e.g., centered on or near the molars). Alternatively or additionally, the user may manually adjust the light intensity in the torch mode, e.g., by adjusting a slider on the screen of the device or by one or more buttons on the side of the device.

Similarly, the exposure time for the camera may be adjusted based on the amount of light within all or a portion of the overly region of the imaging field. Controlling the image exposure and/or the depth of field scope for the image may be guided by the region within the overlay. For example, the apparatus (e.g., a non-transitory, computer-readable storage medium storing a set of instructions capable of being executed by a processor of a mobile telecommunications device having a camera) may control the camera so that any auto-exposure function of the camera is modified to base the exposure on a targeted point or region within the overlay. The depth of field may also be adjusted by the apparatus.

The exposure time may be set automatically based on a region within the overlay, as mentioned above. The region within the overlay used for setting the exposure may be different from a region used to set either the focus or the light intensity. In addition, these regions may be different for different views. For example, in anterior images, the focus may be set using a region within the overlay that is on the front (e.g. incisor) teeth, as shown in FIG. 12A, while the region for setting the illumination (e.g., light intensity) may be set based on more anterior teeth (e.g., molars, premolars, etc.) and the region used for setting the exposure may be the same as either the region for setting the focus, the same as the region for setting the illumination, or may be different from either of these. In some variations, all three regions may be the same.

Cheek Retractor Detection

Figure 14B:
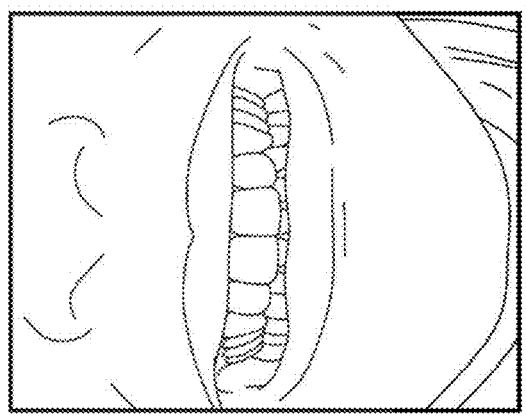
FIG. 14B shows a patient retracting their cheeks without the aid of a finer or retractor.
Figure 14A:
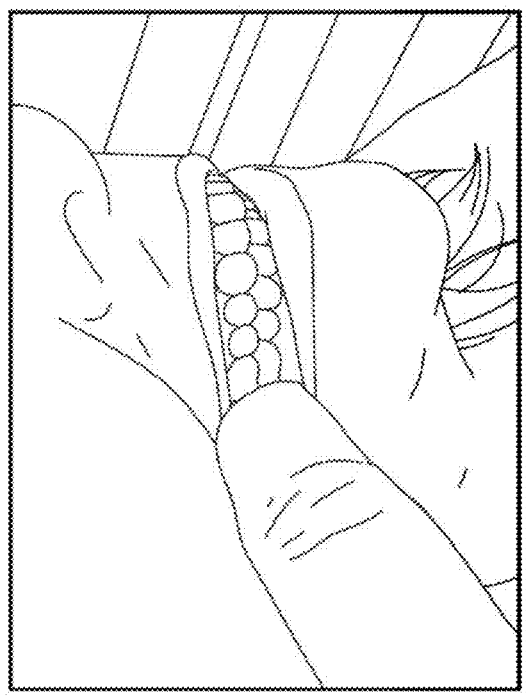
FIG. 14A shows an example of a patient manually retracting their cheek.

Any of the methods and apparatuses (e.g., systems) described herein may include a check retractor and/or the automatic detection of a cheek retractor. For example, the apparatuses and methods described herein may avoid having a user take a patient's images of the predetermined views without using a cheek retractor, particularly when the predetermined views benefit from the use of a cheek retractor. FIG. 14A illustrates an example of a right buccal view of a patient manually retracting (using a finger) their right cheek. Such images may be useful, and indeed multiple such images may be taken and combined (by image stitching) together, e.g., by pulling or manually retracting the cheek from different angles and combining the different images to show as much of the buccal view as possible, including the upper and lower teeth. However, in some variations, it may be beneficial to use a mechanical cheek retractor, such as the one shown in FIG. 14C. This may allow more of the teeth to be visible than would be possible either manually retracting the checks (as shown in FIG. 14A) or simply pulling the lips and cheeks back using the facial muscles, as shown in FIG. 14B.

The apparatuses and methods described herein may remind the user to use cheek retractors before taking intraoral photos, as described above (e.g., using an alert window, etc.). However, the user (who may be the patient) may choose not to, leading to images for the intra-oral predetermined views in particular that are not optimal, and may be harder to process. In some variations, the apparatus or method may automatically detect if a check retractor is present and may warn the user when they are not detected. For example machine learning may be used to train the apparatus to automatically detect a cheek retractor. Alternatively or additionally, the cheek retractor may include one or more markings on the check retractor in visible regions that may be readily detected. The markings (e.g., dots, bar codes, QR codes, text, patterns, icons, etc.) may be detected by the apparatus and may also be used to help automatically identify the position of the patient, and therefore which predetermined view (e.g., which predetermined view overlay) should be used or is being taken.

Figure 14C:
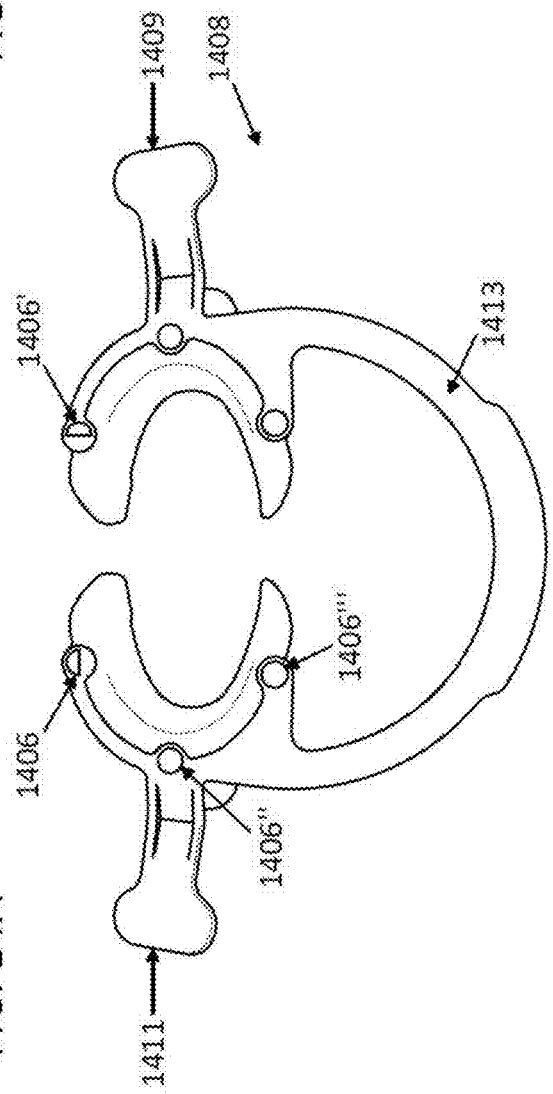
FIG. 14C is an example of a cheek retractor that may be used to aid in retracting the cheeks.

In the exemplary device shown in FIG. 14C, the cheek retractor 1408 includes a plurality (in this example, six) of markings 1406, 1406', 1406", 1406' on the outer surface that will be visible when imaging the patient wearing the cheek retractor. The markings may be on the outer and upper surface, which will be over the patient's lips when worn. The unitary cheek retractor shown has a left side with a patient handle 1409 that is connected via a flexible bridge region 1413 to a right side with a second patient handle 1411. The patient-facing side includes a channel or groove for holding the lips and cheeks and the bridge region may apply a force to separate the left and right side, holding the cheeks open, exposing the teeth. The cheek retractor may be colored (e.g., may include color dots) for identifying the orientation of the patient's teeth when worn. In the example shown in FIG. 14C, two of the markings 1406, 1406' have different orientation markers, shown as a horizontal line on one 1406 and a vertical line on the other 1406' (the line may be formed by the flat edge of the semicircular shape forming the marking). These orientation markers may be formed in to the device, or they may be printed on it. I some variations the markings may be different colors and/or shapes, and may therefore provide orientation and/or distance information. For example, the marking(s) may be used to determine the distance between the patient (or the retractor device) and the camera. As mentioned herein, the method and/or apparatus may determine an estimate of distance from the size of an individual marker and/or from the spacing between different markings in the resulting image. In general, it may be desired to take any of the intraoral images with the camera between about 6 and about 16 inches from the patient's mouth (e.g., between about 7 and 14 inches, between about 8 and 12 inches, etc.). As mentioned, if the distance is outside of this predefined range, the apparatus may instruct the user to adjust the position (e.g., move closer or farther, etc.). Similarly, the apparatus may center the image using the markings, so that the teeth (or a portion of the teeth) are centered within the image(s).

The markings on the retractor may also be used to aid in automatically cropping the images.

Figure 15:
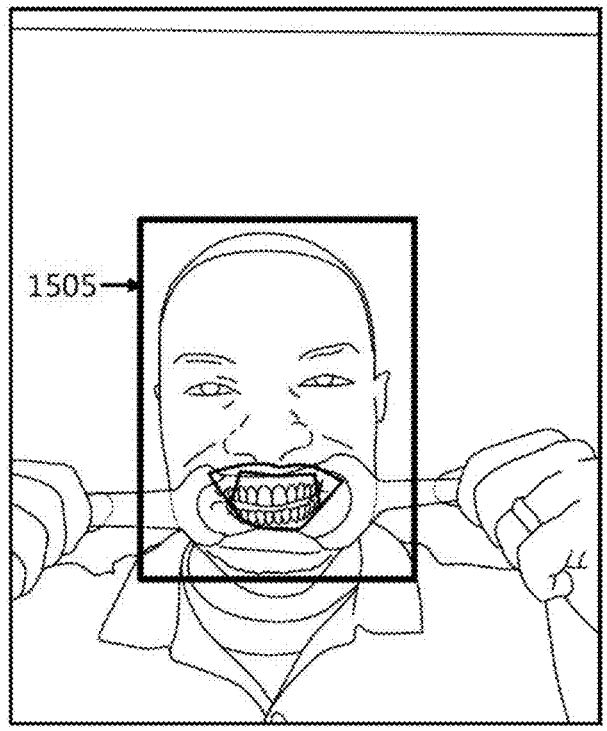
FIG. 15 is an example of a view of a patient using a retractor.
Figure 16:
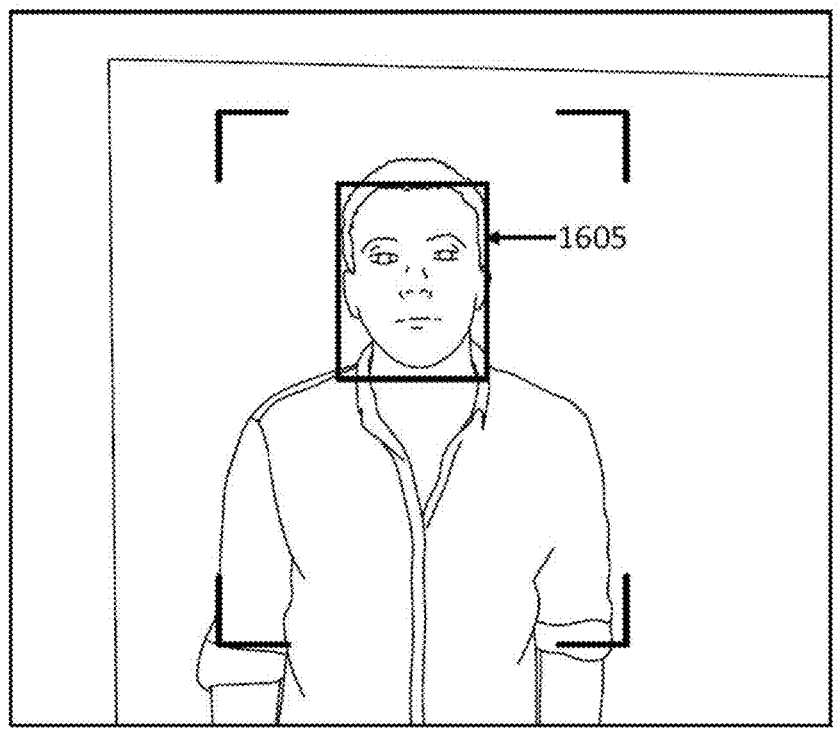
FIG. 16 shows a patient for which facial recognition may be used to provide information about the images.

Any of the apparatuses and methods described herein may also estimate between the patient and the camera of the mobile telecommunications device. For example, any of these methods and apparatuses may facial detection from the image to identify the patient's face; once identified, the size and position of the face (and/or any landmarks from the patient's face, such as eyes, nose, ears, lips, etc.) and may determine the approximate distance to the camera. This information may be used to guide the user in positioning the camera; e.g., instructing the user to get closer or further from the patient in order to take the images as described above. For example, in FIG. 15, the box 1505 on the screen identifies the automatically detected face/head of the patient; the face was identified using the face identification software available from the developer. FIG. 16 shows another example of face identification. In both examples, the method and apparatus may determine that the camera is too far away by comparing the size of the recognized face (the box region) to the size of the field. In both cases, the user may be provided instructions (audible, visual, text, etc.) to move the camera closer. In FIG. 15, the image to be taken is an anterior view of the teeth, and the user may be instructed to move much closer to focus on the teeth. In FIG. 16, the view may be a face (nonsmiling) image of the patient, and the user may be instructed to get closer. The distance to the patient may be estimated in any appropriate manner. For example, the distance may be derived from the size of the rectangle made around the patient's face or mouth, as mentioned (e.g., if it is too small, the camera is too far). The size of the 'box' identifying the face may be absolute (e.g., must be above a set value) or as a percent of the image field size.

The distance from the camera may be approximate using other identified features, as mentioned, including the eye separation distance (pupil separation distance, etc.) when these features are visible. Any of these distance estimates may be stored with the image for later use, e.g., in estimating size or projecting three-dimensional features.

Also described herein is the use of continuous imaging (shooting) of the teeth. For example, rather than taking individual images, e.g., one at a time, the apparatus or method may be configured to general patient photos by using a continuous shooting mode. A rapid series of images may be taken while moving the mobile device. Movement can be guided by the apparatus, and may be from left to right, upper to lower, etc. From the user's perspective it may be similar to taking a video, but a series of images (still images) may be extracted by the apparatus. For example, the apparatus may automatically review the images and match (or approximately match) views to the predetermined views, e.g., using the overlays as described above. The apparatus may select only those images having a sufficiently high quality. For example, blurry, dark or not optimally positioned photos may be automatically rejected. Similarly, multiple photos may be combined (by stitching, averaging, etc.).

In some variations, the user may be patient, and the apparatus may be configured to allow the user to take continuous "selfies" in this manner. For example, a continuous shooting mode may allow the patient to take photos of their smile alone with the camera (e.g., a back-facing camera). The apparatus may use face and/or smile detection to guide patient and indicate if the camera is well positioned. In variations in which the screen is not facing the user, the apparatus may be configured to provide a user-detectable output (e.g., a flash, sound or the like) indicating that the patient should start moving the device around their head/mouth and may indicate that they should move the camera closer or further, to the right/left, up/down, etc. For example, an indicator such as light (e.g., flash) or sound (a voice or tone, etc.) may be used as an indicator. For example, a flashing and/or sound may be used to indicate to patient when to start moving mobile device, and the apparatus may start taking photos in the continuous mode (also referred to as a burst mode) and move the mobile device in the indicated direction.

As mentioned above, any of these variations may include detection of the teeth automatically, e.g., by machine learning. Detection of the patient teeth automatically may improve photo quality. In some variations, the machine learning (e.g., the machine learning framework provided by Apple with iOS 11) may be used to detect the presence of teeth when photos are taken, and to further guide the user. For example, the user may be alerted when the teeth are not visible, or to automatically select which predetermined view overly to use, to indicate if the angle is not correct, to indicate that the user is too close or too far from the patient, etc.

In general, in addition to the images captured by the apparatus, additional information, including the orientation and location of the camera relative to the patient, may be extracted from the sequence of images taken from a continuous shooting described above. For example, positional information, including the relative distance and/or angle that the camera is relative to the patient's mouth, may be extracted from the time sequence. Additional information, such as motion sensors (e.g., accelerometers, etc.) in the mobile telecommunications device, may be used as well. This additional sensor information (e.g., accelerometer, angle, etc.) information may be provided with the images. Such information may be helpful in both guiding the user, e.g., in instructing the user to get closer/farther, move more slowly, etc., but also in calculating dimensional information (e.g., size, three-dimensional position and/or surface or volumetric information, etc.).

Pre-Screening for Orthodontic Treatment

As mentioned above, in general, the apparatuses and methods described herein may be used to remotely pre-screen a patient for an orthodontic treatment. For example, the methods described herein may include, and/or may be used to determine if a patient would benefit from an orthodontic correction procedure to orthodontically move and straighten the patient's teeth using, e.g., a series of dental aligners. These methods and apparatuses may be part of a case assessment tool. The user (a dental professional or in some cases the potential patient) may be guided to take a set of predetermined views as described above, and these views may be transmitted (e.g., uploaded) from the mobile telecommunications device to a remote location. At the remote location, which may include a server, the images may be processed manually, automatically or semi-automatically to determine if the patient is a candidate for the orthodontic procedure.

The series of predetermined views described herein may be used to determine if a patient is a good candidate by identifying (manually or automatically) the amount and extent of movement of teeth required in order to straighten the teeth. Patients requiring excessive tooth movement may be indicated as not a candidate. Patient requiring surgical treatment (e.g., patients requiring palatal expansion, etc.) may be indicated as not a candidate. In some variations patients requiring tooth extraction and/or interproximal reduction may be indicated as not a candidate, at least for some orthodontic treatments. In variations, rather than simply determining that a patient is a candidate or not a candidate for a particular orthodontic treatment, the apparatus or method may instead indicate which type of orthodontic treatment would be best.

These methods may be used to pre-screen for any type of orthodontic treatment, as mentioned, including (for example), teeth straightening using one or a series of temporary aligners (e.g., which may be changed regularly, e.g., weekly). The type of orthodontic treatment may be limited to relatively easy orthodontic straightening procedures, such as orthodontic treatments with aligners that may take less than x months to complete (e.g., 1 month or less, 2 months or less, 3 months or less, 4 months or less, etc.).

Either before, during or after capturing the series of images, any of these methods and apparatuses may be configured to collect information about the patient, as discussed above. In addition to, or instead of, patient-identification information, the apparatus may also include information about the patient and/or user's chief orthodontic concern for the patient's teeth (e.g., tooth crowding, tooth spacing, smile width/arch width, smile line, horizontal overjet, vertical overbite, cross bite, bite relationship, etc.). The apparatus may include a menu of these concerns and may allow the user (dental professional and/or patient) to select one or more of them, or enter their own. The one or more chief dental concerns may be added to the set or series of images from the predetermined views. For example, the chief dental concern(s) may be appended or combined with the set or series of images, and transmitted to the remote site and used to determine if the patient is a good candidate for a particular orthodontic procedure.

In general, the images may be used to quantify and/or model the position of the patient's teeth. The position and orientation of the patients teeth, relative to the other teeth in the dental arch or the opposite dental arch, may provide an estimate of the movement or procedures necessary to correct (e.g., align) the patients teeth, or in some variations, the progress of an ongoing treatment.

The methods described herein, may also include monitoring a patient undergoing an orthodontic treatment. For example, the steps of guiding the user, with the same or a different mobile telecommunications device having a camera, to take a series of images of the patient's teeth from the plurality of predetermined views (e.g., by sequentially displaying, on a screen of the mobile telecommunications device, an overlay comprising an outline of teeth in each of the predetermined views) may be repeated during an orthodontic treatment in order to monitor the treatment. Images taken prior to treatment may be compared with images taken during or after treatment.

In any of the methods an apparatuses described herein, the images may be uploaded to a remote server, or storage facility, or they may be kept local to the mobile telecommunications device. When maintained locally on the mobile device, any copies sent remotely for analysis may be destroyed within a predetermined amount of time (e.g., after analysis is complete), so that no additional copies are sent. The images and any accompanying information may generally be encrypted.

As mentioned, any of the methods and apparatuses described herein may be configured for automatic detection of a mirror, such as a dental mirror, used to take any of the images. For example, the apparatus may be configured to identify that the image is a reflection, or to identify a marker on the mirror. A reflection may be determined by identifying a discontinuity (e.g., a line) at the edge(s) of the mirror, and/or the mirror-imaged/inverted images of parts of the image, such as the teeth. When a mirror is detected, the apparatus may display a mirror icon (or may indicate on the mirror icon. In some variations the image resulting may be inverted (mirrored) so that the image is in the same orientation as it would be had a mirror not been used.

The images (e.g., the predetermined series of images) may be used to supplement additional information (e.g., scans, 3D models, etc.) of the patient's teeth. Images taken as described herein may provide information on the shape, location and/or orientation of the patient's teeth and gingiva, including information related to the patient's root. Thus, this information may be used in conjunction with other images or models, including 3D models (e.g., digital models) of the patient's teeth, and may be combined with, or may supplement this information.

Various embodiments of the disclosure further disclose a non-transitory, computer-readable storage medium storing a set of instructions capable of being executed by a processor of a mobile telecommunications device, that, when executed by the processor, causes the processor to display real-time images of the patient's teeth on a screen of the mobile telecommunications device, display an overlay comprising an outline of teeth in a predetermined view atop the images of the patient's teeth, and enable capturing of an image of the patient's teeth. For example, the non-transitory, computer-readable storage medium, wherein the set of instructions, when executed by the processor, can further cause the processor to display a generic overlay. For another example, the non-transitory, computer-readable storage medium, wherein the set of instructions, when executed by the processor, can further cause the processor to display a patient-specific overlay derived from the patient's teeth.

For example, the non-transitory, computer-readable storage medium, wherein the set of instructions, when executed by the processor, can further cause the processor to automatically trigger an indicator when the overlay approximately matches with the patient's teeth. For example, the non-transitory, computer-readable storage medium, wherein the set of instructions, when executed by the processor, can further cause the processor to estimate an indicator of the distance between an edge of the patient's teeth in the view of the patient's teeth and to trigger the indicator when the outline of teeth in the overlay is less than or equal to a threshold value. For example, the non-transitory, computer-readable storage medium, wherein the set of instructions, when executed by the processor, can further cause the processor to estimate an indicator of the distance between an edge of the patient's teeth at two or more regions in the view of the patient's teeth and to trigger the indicator when the outline of teeth in the overlay is less than or equal to a threshold value. For example, the non-transitory, computer-readable storage medium, wherein the set of instructions, when executed by the processor, can further cause the processor to trigger the indicator by displaying a visual indicator on the screen.

In general, various embodiments of the disclosure further disclose a non-transitory, computer-readable storage medium storing a set of instructions capable of being executed by a processor of a mobile telecommunications device, that, when executed by the processor, causes the processor to display real-time images of the patient's teeth on a screen of the mobile telecommunications device and display an overlay comprising a cropping frame and an outline of teeth in one of an anterior view, a buccal view an upper jaw view, or a lower jaw view, wherein the overlay is displayed atop the images of the patient's teeth, and enable capturing of an image of the patient's teeth. The non-transitory, computer-readable storage medium, wherein the set of instructions, when executed by the processor, can further cause the processor to review the captured image and indicate on the screen if the captured image is out of focus and automatically crop the captured image as indicated by the cropping frame.

For example, the non-transitory, computer-readable storage medium, wherein the set of instructions, when executed by the processor, can further cause the processor to check the image quality of the captured image and displaying on the screen if the image quality is below a threshold for image quality. For example, the non-transitory, computer-readable storage medium, wherein the set of instructions, when executed by the processor, can further cause the processor to automatically crop the captured image based on a cropping outline displayed as part of the overlay. For example, the non-transitory, computer-readable storage medium, wherein the set of instructions, when executed by the processor, can further cause the processor to transmit the captured image to a remote server.

For example, the non-transitory, computer-readable storage medium, wherein the set of instructions, when executed by the processor, can further cause the processor to display an overlay comprising an outline of teeth in a predetermined view such as an anterior view, a buccal view an upper jaw view, or a lower jaw view. For example, the non-transitory, computer-readable storage medium, wherein the set of instructions, when executed by the processor, can further cause the processor to repeat the steps of viewing, displaying, moving and capturing to capture anterior, buccal, upper jaw and lower jaw images of the patient's teeth. For example, the non-transitory, computer-readable storage medium, wherein the set of instructions, when executed by the processor, can further cause the processor to capture an image of a patient's identification using the mobile telecommunications device and automatically populate a form with user identification information based on the imaged identification. For example, the non-transitory, computer-readable storage medium, wherein the set of instructions, when executed by the processor, can further cause the processor to display instructions on positioning the patient's teeth on the screen of the mobile telecommunications device prior to displaying the overlay.

The systems, devices, and methods of the preferred embodiments and variations thereof can be embodied and/or implemented at least in part as a machine configured to receive a computer-readable medium storing computer-readable instructions. The instructions are preferably executed by computer-executable components preferably integrated with the system including the computing device configured with software. The computer-readable medium can be stored on any suitable computer-readable media such as RAMs, ROMs, flash memory, EEPROMs, optical devices (e.g., CD or DVD), hard drives, floppy drives, or any suitable device. The computer-executable component is preferably a general or application-specific processor, but any suitable dedicated hardware or hardware/firmware combination can alternatively or additionally execute the instructions.

EXAMPLES

In one example, described herein is a photo uploading mobile app (control software) that may be installed on a mobile device such as a smartphone and may control the smartphone camera to take dental images of a patient in a particular manner. The particular manner may include a specific sequence of photos, as well as controlling the image quality and/or imaging characteristics in order to more accurately plan or track a therapeutic treatment, e.g., of a series of dental aligners.

For example, the application ("app") may be configured to require login (username, password) in order to use. Alternative logins (e.g., fingerprint, passcode, etc.) may be used to login. Once logged in, the app may present a list of patients and/or may allow patients to be added. The user may select or add a patient, e.g., from a selectable list that is displayed. Adding a patient may include entering identifying information about the patient (e.g., first name, last name, date of birth, location such as country, city, state, zip code, etc., and gender. Thereafter, the app may guide the doctor or clinician in taking a predetermined series of images, such as those shown in FIG. 5A, and described above.

For existing patients, the app may allow the user to view photos that were already taken and/or begin taking new photos. Thus, any of the apparatuses (including apps) described herein may allow the user to take the requested series of images (which may depend on the patient identity, treatment plan, etc.) and may include taking additional images (e.g., 3 or more, 4 or more, 5 or more, 6 or more, 7 or more, 8 or more, 9 or more, 10 or more, 11 or more, 12 or more, etc.). For each patient, photos may be taken at different times, showing the progression of treatment. For example, a series of photographs (such as those shown in FIG. 5A) may be taken prior to treatment, and one or more times during treatment, and/or post-treatment. Additional photos may be taken at any of these times as well. When the user is taking photographs in the series, the app may guide the user in taking patient photos from the predetermined series, and may display on the screen one or more outlines (including outlines of a typical set of teeth, head/face, etc., as described above). The app may also guide the user in applying assistance devices, such as a retractor and/or dental mirror. Once the image is taken, the app may be pre-cropped and/or cropped manually by the user. The app may also examine the content of the image to confirm focus, subject matter (angle, etc.) illumination, etc. The app may prompt the user to re-take and/or save the image(s).

Images/photos taken may be uploaded by the apparatus into a remote server or site, and stored for later retrieval by the physician and/or transmission to a third party along with patient and/or physician identifying information, and/or information about when they were taken. The physicians may approve or review the images using the app, or using another computer accessing the remote site. Images may be individually uploaded, or they may be uploaded as a composite of multiple separate images.

A physician may also comment and/or append comments, on the images or to accompany the images. In any of these apparatuses, the app may also provide access to patient case management software including modeling and 3D images/rendering of the patient's teeth.

The app may also include instructions (e.g., a frequently asked questions portion, a tutorial, etc.).

In some variations, the physician may mark or otherwise signify that a particular patient or case be processed by a remote server, e.g., for clinical assessment, and/or to prepare a series of aligners. As mentioned above, the app may be used on any mobile device having or communicating with a camera, such as a smartphone, smartwatch, pad, etc.

Although the examples described herein are specifically described as being for use with a mobile telecommunication device (such as a smartphone, pad, etc.), in some variations these methods and apparatuses implementing them may be performed with devices that include display and a processor that ae not limited to mobile telecommunications devices. For example, the methods and apparatuses may be configured for use with a virtual reality (VR)/augmented reality (AR) headset or any other imaging device that may transmit images (e.g., photos) directly to a computer via a direct connection (e.g., cable, dedicated wireless connection, etc.), and/or may save the images to removable or transferrable memory (e.g., an SD card); the image data could then be uploaded to a remote server via another device. Thus, any of the methods and apparatuses described herein which recite or refer to a mobile telecommunications device may be performed with an imaging device.

For example, a method for remotely pre-screening a patient for an orthodontic treatment may include: guiding a user, with an imaging device having a camera, to take a series of images of the patient's teeth in a plurality of predetermined views, transmitting the series of images from the imaging device to a remote location to determine if the patient is, or is not, a candidate for the orthodontic treatment based on the series of images; and displaying, on a screen, an indicator that the patient is, or is not, a candidate for the orthodontic treatment.

Similarly, a method for remotely pre-screening a patient for an orthodontic treatment may include: guiding a user, with an imaging device having a camera, to take a series of images of the patient's teeth from a plurality of predetermined views by sequentially displaying, on a screen of the imaging device, an overlay comprising an outline of teeth in each of the predetermined views; receiving, in the imaging device, an indication of the patient's chief dental concern; aggregating, in the imaging device, the series of images and the chief dental concern; transmitting the aggregated series of images and the chief dental concern to a remote location to determine if the patient is a candidate for the orthodontic treatment based on the series of images; and displaying, on the screen of the imaging device or a device in communication with the imaging device, an indicator that the patient is, or is not, a candidate for the orthodontic treatment.

As another example, a system for remotely pre-screening a patient for an orthodontic treatment, may include: a non-transitory, computer-readable storage medium storing a set of instructions capable of being executed by a processor of an imaging device having a camera, that, when executed by the processor, causes the processor to: guide a user to take a series of images of the patient's teeth in a plurality of predetermined views with the camera; transmit the series of images from the imaging device to a remote location to determine if the patient is a candidate for the orthodontic treatment based on the series of images; and display, on a screen of the imaging device or a device in communication with the imaging device, an indicator that the patient is, or is not, a candidate for the orthodontic treatment.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A non-transitory, computer-readable storage media having executable instructions that are executed by a processor of a mobile telecommunications device to cause the mobile telecommunications device having a camera to perform a method for capturing dental images for analysis, the method comprising:

guiding a patient to capture, with the camera of the mobile telecommunications device, a first predetermined set of images of teeth of the patient at specified viewing angles relative to the teeth using a first indicator that is output from the mobile telecommunications device, wherein the first indicator indicates to the patient that the patient should move the mobile telecommunications device relative to a mouth of the patient to the right/left with the jaws closed, in order to capture the first predetermined set of images of teeth at the specified viewing angles;

guiding the patient to capture, with the camera of the mobile telecommunications device, a second predetermined set of images of teeth of the patient at specified viewing angles relative to the teeth using a second indicator output from the mobile telecommunications device, wherein the second indicator indicates to the patient that the patient should move the mobile telecommunications device relative to the mouth of the patient to the right/left with the jaws open, in order to capture the second predetermined set of images of teeth at the specified viewing angles; and capturing the first and second predetermined sets of images of the teeth of the patient as the patient moves the camera of the mobile telecommunications device relative to the mouth of the patient;

displaying, during the capture of the first and second predetermined sets of images of the teeth of the patient, video from the camera of the mobile telecommunications device to a screen of the mobile telecommunications device;

uploading the captured first and second predetermined sets of images of the teeth for treatment progress evaluation to provide a treatment progress evaluation of the patient.

2. The non-transitory, computer-readable storage media of claim 1, wherein the captured first and second predetermined sets of images of the teeth are uploaded to a remote server.

3. The non-transitory, computer-readable storage media of claim 1, wherein the patient is guided to capture the first and second predetermined sets of images in a predetermined sequence.

4. The non-transitory, computer-readable storage media of claim 1, wherein the method further comprises recognizing and categorizing the teeth imaged by the camera of the mobile telecommunications device based on training.

5. The non-transitory, computer-readable storage media of claim 1, wherein the method further comprises automatic detection of teeth imaged by the camera of the mobile telecommunications device by machine learning.

6. The non-transitory, computer-readable storage media of claim 1, wherein the method further comprises detecting, using edge detection image processing, the teeth imaged by the camera of the mobile telecommunications device.

7. The non-transitory, computer-readable storage media of claim 1, wherein capturing the first and second predetermined sets of images of the teeth of the patient as the patient moves the camera of the mobile telecommunications device relative to the mouth of the patient comprises detecting the teeth of the patient and automatically focusing the camera of the mobile telecommunications device on the detected teeth.

8. The non-transitory, computer-readable storage media of claim 1, wherein capturing the first and second predetermined sets of images of the teeth of the patient as the patient moves the camera of the mobile telecommunications device relative to the mouth of the patient comprises automatically adjusting an illumination provided by a light source of the mobile telecommunications device.

9. The non-transitory, computer-readable storage media of claim 8, wherein the illumination provided by the light source of the mobile telecommunications device is adjusted to be a continuously on light.

10. The non-transitory, computer-readable storage media of claim 1, wherein the specified viewing angles comprise an upper and lower jaw anterior viewing angle with a closed bite, a right buccal viewing angle with the closed bite, a left buccal viewing angle with the closed bite, an anterior viewing angle with an open bite, a right buccal viewing angle with the open bite, and a left buccal viewing angle with the open bite, and wherein first indicator and the second indicator comprise a first overlay and second overlay, respectively, displayed to the screen of the mobile telecommunications device, the first overlay associated with the upper and lower anterior viewing angle with the closed bite, and the second overlay associated with the anterior viewing angle with the open bite.

11. The non-transitory, computer-readable storage media of claim 10, wherein the first and second overlays are displayed on the screen as solid.

12. The non-transitory, computer-readable storage media of claim 10, wherein the first and second overlays are displayed on the screen as transparent.

13. The non-transitory, computer-readable storage media of claim 10, wherein the first and second overlays are displayed on the screen as an outline of teeth.

14. The non-transitory computer-readable storage media of claim 1, wherein capturing the first and second predetermined sets of images of the teeth of the patient as the patient moves the camera of the mobile telecommunications device relative to the mouth of the patient comprises detecting one or more teeth imaged by the camera of the mobile telecommunications device and automatically taking an image when the detected one or more teeth are in a desired orientation, size, and/or location on the screen.

15. The non-transitory computer-readable storage media of claim 14, wherein capturing the first and second predetermined sets of images of the teeth of the patient as the patient moves the camera of the mobile telecommunications device relative to the mouth of the patient comprises using an overlay.

16. The non-transitory computer-readable storage media of claim 14, wherein capturing the predetermined set of images of the teeth of the patient as the patient moves the camera of the mobile telecommunications device relative to the mouth of the patient is performed without an overlay.

17. The non-transitory, computer-readable storage media of claim 1, wherein, after capturing the first and second predetermined sets of images of the teeth, an image quality of the captured first and second predetermined sets of images is reviewed and an indication is displayed on the screen if image quality of one or more of the captured first and second predetermined sets of images is below a threshold.

18. The non-transitory, computer-readable storage media of claim 17, wherein the image quality comprises a focus.

19. The non-transitory, computer-readable storage media of claim 17, wherein the image quality comprises a lighting.

20. The non-transitory, computer-readable storage media of claim 17, wherein the image quality comprises a visibility of all the teeth and wherein image recognition algorithms are used to review of the first and second predetermined sets of images to assess the visibility of all the teeth.

21. The non-transitory, computer-readable storage media of claim 17, wherein the method further comprises showing a message on the screen of the mobile telecommunications device to the patient to retake an alternative image if the image quality of one or more of the captured first and second predetermined sets of images is below the threshold.

22. The non-transitory, computer-readable storage media of claim 1, wherein, after capturing the first and second predetermined sets of images of the teeth, the first and second predetermined sets of images of the teeth are automatically labeled with a corresponding view that is detected.

23. The non-transitory, computer-readable storage media of claim 1, wherein capturing the first and second predetermined sets of images of the teeth of the patient as the patient moves the camera of the mobile telecommunications device relative to the mouth of the patient comprises using the camera in a continuous burst mode.

24. The non-transitory, computer-readable storage media of claim 23, wherein capturing the first and second predetermined sets of images of the teeth of the patient as the patient moves the camera of the mobile telecommunications device relative to the mouth of the patient using the camera in the continuous burst mode comprises automatically reviewing captured images.

25. The non-transitory, computer-readable storage media of claim 24, wherein capturing the first and second predetermined sets of images of the teeth of the patient as the patient moves the camera of the mobile telecommunications device relative to the mouth of the patient using the camera in the continuous burst mode comprises automatically matching views to the specified viewing angles.

26. The non-transitory, computer-readable storage media of claim 24, wherein automatically reviewing captured images comprises selecting only those images having a sufficiently high quality for the first and second predetermined sets of images of the teeth.

27. The non-transitory, computer-readable storage media of claim 1, wherein guiding the patient to capture the first and second predetermined sets of images of teeth of the patient at specified viewing angles relative to the teeth comprises displaying one or more arrows on the screen of the mobile telecommunications device, the one or more arrows indicating that a user should move the mobile telecommunications device in a particular direction.

28. The non-transitory, computer-readable storage media of claim 1, wherein the method further comprises displaying a message guiding the patient to take the first and second predetermined sets of images of the teeth of the patient with a retractor on the screen of the mobile telecommunications device.

29. A non-transitory, computer-readable storage media having executable instructions that are executed by a processor of a mobile telecommunications device to cause the mobile telecommunications device having a camera to perform a method for capturing dental images for analysis, the method comprising:
  guiding a patient to capture, with the camera of the mobile telecommunications device following retraction of the patient's cheeks, a first predetermined set of images of teeth of the patient at specified viewing angles relative to the teeth using a first indicator that is output from the mobile telecommunications device, the specified viewing angles comprising an upper and lower jaw anterior viewing angle with a closed bite, a right buccal viewing angle with the closed bite, and a left buccal viewing angle with the closed bite, and wherein the first indicator indicates to the patient that the patient should move the mobile telecommunications device relative to a mouth of the patient to capture the first predetermined set of images of teeth at the specified viewing angles in a continuous mode;
  guiding the patient to capture a second predetermined set of images of teeth of the patient at specified viewing angles relative to the teeth using a second indicator that is output from the mobile telecommunications device, the specified viewing angles comprising an anterior viewing angle with an open bite, a right buccal viewing angle with the open bite, and a left buccal viewing angle with the open bite, and wherein the second indicator indicates to the patient that the patient should move the mobile telecommunications device relative to a mouth of the patient to capture the second predetermined set of images of teeth at the specified viewing angles in the continuous mode;
  capturing the first and second predetermined sets of images of the teeth of the patient as the patient moves the mobile telecommunications device relative to the mouth of the patient;
  displaying, during the capture of the first and second predetermined sets of images of the teeth of the patient, video from the camera of the mobile telecommunications device to a screen of the mobile telecommunications device;
  uploading the captured first and second predetermined sets of images of the teeth for treatment progress evaluation.

30. A non-transitory, computer-readable storage media having executable instructions that are executed by a processor of a mobile telecommunications device to cause the mobile telecommunications device having a camera to perform a method for capturing dental images for analysis, the method comprising:
  guiding a patient to capture, with the camera of the mobile telecommunications device, a first predetermined set of images of teeth of the patient at specified viewing angles relative to the teeth using an indicator that is output from the mobile telecommunications device, wherein the user-detectable output indicates to the patient that the patient should move the mobile telecommunications device relative to a mouth of the patient anteriorly to buccally with the teeth closed, in order to capture the first predetermined set of images of teeth at the specified viewing angles;
  guiding the patient to capture, with the camera of the mobile telecommunications device, a second predetermined set of images of teeth of the patient at specified viewing angles relative to the teeth using an indicator that is output from the mobile telecommunications device, wherein the user-detectable output indicates to the patient that the patient should move the mobile telecommunications device relative to a mouth of the patient anteriorly to buccally with the teeth open, in order to capture the second predetermined set of images of teeth at the specified viewing angles;
  capturing the first and second predetermined sets of images of the teeth of the patient as the patient moves the mobile telecommunications device relative to the mouth of the patient;
  displaying, during the capture of the first and second predetermined sets of images of the teeth of the patient, video from the camera of the mobile telecommunications device to a screen of the mobile telecommunications device, wherein the screen is not facing the patient during capture of the first and second predetermined sets of images;
  after capturing the first and second predetermined sets of images of the teeth, reviewing an image quality of the captured first and second predetermined sets of images, wherein the image quality comprises a visibility of all or a sub-set of the teeth and wherein image recognition algorithms are used to review of the predetermined set of images to assess the visibility of all or a sub-set of the teeth; and
  displaying on the screen of the mobile telecommunications device a result of the image quality review; and
  uploading the captured first and second predetermined sets of images of the teeth for treatment progress evaluation wherein the teeth are automatically recognized and categorized based on machine learning.

* * * * *